US012667307B2

(12) United States Patent
Al-Ali et al.

(10) Patent No.: US 12,667,307 B2
(45) Date of Patent: Jun. 30, 2026

(54) HYDRATION MEASUREMENT USING OPTICAL SENSORS

(71) Applicant: Masimo Corporation, Irvine, CA (US)

(72) Inventors: Ammar Al-Ali, San Juan Capistrano, CA (US); Walter M. Weber, Laguna Hills, CA (US); Sean Devlin, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 414 days.

(21) Appl. No.: 18/317,435

(22) Filed: May 15, 2023

(65) Prior Publication Data

US 2023/0371893 A1 Nov. 23, 2023

Related U.S. Application Data

(60) Provisional application No. 63/373,987, filed on Aug. 30, 2022, provisional application No. 63/364,866, filed on May 17, 2022.

(51) Int. Cl.
*A61B 5/00* (2006.01)

(52) U.S. Cl.
CPC .......... *A61B 5/4875* (2013.01); *A61B 5/6802* (2013.01); *A61B 5/7435* (2013.01); *A61B 2562/0238* (2013.01)

(58) Field of Classification Search
CPC ... A61B 5/4875; A61B 5/6802; A61B 5/7435; A61B 2562/0238; A61B 5/681; A61B 5/1455; A61B 5/0075; A61B 5/0077; A61B 5/443
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |

(Continued)

FOREIGN PATENT DOCUMENTS

| | | |
|---|---|---|
| CN | 107 106 051 | 8/2017 |
| WO | WO 2017/132404 | 8/2017 |
| WO | WO 2023/225484 | 11/2023 |

OTHER PUBLICATIONS

US 2024/0016391 A1, 01/2024, Lapotko et al. (withdrawn)

(Continued)

*Primary Examiner* — Patrick Fernandes
(74) *Attorney, Agent, or Firm* — Knobbe, Martens, Olson & Bear, LLP

(57) ABSTRACT

The present disclosure provides a physiological monitoring system that can include a hardware processor. The hardware processor can access first optical data corresponding to a water-dependent radiation wavelength attenuated through a medium and detected at a detector. The hardware processor can access second optical data corresponding to a water-independent radiation wavelength attenuated through the medium and detected at the detector. The hardware processor can determine a hydration index of the medium based on the first and second optical data.

20 Claims, 9 Drawing Sheets

(56) References Cited

U.S. PATENT DOCUMENTS

| | | | |
|---|---|---|---|
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,088,607 A | 7/2000 | Diab et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,421,549 B1 * | 7/2002 | Jacques .............. G01N 21/3151 |
| | | 600/323 |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,650,917 B2 | 11/2003 | Diab et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |

(56)                References Cited

U.S. PATENT DOCUMENTS

| | | | |
|---|---|---|---|
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,761,127 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| RE41,912 | E | 11/2010 | Parker |
| 7,880,626 | B2 | 2/2011 | Al-Ali et al. |
| 7,909,772 | B2 | 3/2011 | Popov et al. |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,941,199 | B2 | 5/2011 | Kiani |
| 7,957,780 | B2 | 6/2011 | Lamego et al. |
| 7,962,188 | B2 | 6/2011 | Kiani et al. |
| 7,976,472 | B2 | 7/2011 | Kiani |
| 7,990,382 | B2 | 8/2011 | Kiani |
| 8,008,088 | B2 | 8/2011 | Bellott et al. |
| RE42,753 | E | 9/2011 | Kiani-Azarbayjany et al. |
| 8,028,701 | B2 | 10/2011 | Al-Ali et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,130,105 | B2 | 3/2012 | Al-Ali et al. |
| 8,182,443 | B1 | 5/2012 | Kiani |
| 8,190,223 | B2 | 5/2012 | Al-Ali et al. |
| 8,203,438 | B2 | 6/2012 | Kiani et al. |
| 8,203,704 | B2 | 6/2012 | Merritt et al. |
| 8,219,172 | B2 | 7/2012 | Schurman et al. |
| 8,224,411 | B2 | 7/2012 | Al-Ali et al. |
| 8,229,532 | B2 | 7/2012 | Davis |
| 8,233,955 | B2 | 7/2012 | Al-Ali et al. |
| 8,255,026 | B1 | 8/2012 | Al-Ali |
| 8,265,723 | B1 | 9/2012 | McHale et al. |
| 8,274,360 | B2 | 9/2012 | Sampath et al. |
| 8,280,473 | B2 | 10/2012 | Al-Ali |
| 8,315,683 | B2 | 11/2012 | Al-Ali et al. |
| RE43,860 | E | 12/2012 | Parker |
| 8,346,330 | B2 | 1/2013 | Lamego |
| 8,353,842 | B2 | 1/2013 | Al-Ali et al. |
| 8,355,766 | B2 | 1/2013 | MacNeish et al. |
| 8,374,665 | B2 | 2/2013 | Lamego |
| 8,388,353 | B2 | 3/2013 | Kiani et al. |
| 8,401,602 | B2 | 3/2013 | Kiani |
| 8,414,499 | B2 | 4/2013 | Al-Ali et al. |
| 8,418,524 | B2 | 4/2013 | Al-Ali |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,707 | B2 | 6/2013 | Kiani |
| 8,471,713 | B2 | 6/2013 | Poeze et al. |
| 8,473,020 | B2 | 6/2013 | Kiani et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| D692,145 | S | 10/2013 | Al-Ali et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,584,345 | B2 | 11/2013 | Al-Ali et al. |
| 8,588,880 | B2 | 11/2013 | Abdul-Hafiz et al. |
| 8,630,691 | B2 | 1/2014 | Lamego et al. |
| 8,641,631 | B2 | 2/2014 | Sierra et al. |
| 8,652,060 | B2 | 2/2014 | Al-Ali |
| 8,666,468 | B1 | 3/2014 | Al-Ali |
| 8,670,811 | B2 | 3/2014 | O'Reilly |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,702,627 | B2 | 4/2014 | Telfort et al. |
| 8,712,494 | B1 | 4/2014 | Macneish, III et al. |
| 8,715,206 | B2 | 5/2014 | Telfort et al. |
| 8,723,677 | B1 | 5/2014 | Kiani |
| 8,740,792 | B1 | 6/2014 | Kiani et al. |
| 8,755,535 | B2 | 6/2014 | Telfort et al. |
| 8,755,872 | B1 | 6/2014 | Marinow |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,781,544 | B2 | 7/2014 | Al-Ali et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,840,549 | B2 | 9/2014 | Al-Ali et al. |
| 8,852,094 | B2 | 10/2014 | Al-Ali et al. |
| 8,852,994 | B2 | 10/2014 | Wojtczuk et al. |
| 8,897,847 | B2 | 11/2014 | Al-Ali |
| 8,911,377 | B2 | 12/2014 | Al-Ali |
| 8,989,831 | B2 | 3/2015 | Al-Ali et al. |
| 8,998,809 | B2 | 4/2015 | Kiani |
| 9,066,666 | B2 | 6/2015 | Kiani |
| 9,066,680 | B1 | 6/2015 | Al-Ali et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,131,881 | B2 | 9/2015 | Diab et al. |
| 9,138,180 | B1 | 9/2015 | Coverston et al. |
| 9,153,112 | B1 | 10/2015 | Kiani et al. |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,095 | B1 | 12/2015 | Al-Ali |
| 9,218,454 | B2 | 12/2015 | Kiani et al. |
| 9,245,668 | B1 | 1/2016 | Vo et al. |
| 9,267,572 | B2 | 2/2016 | Barker et al. |
| 9,277,880 | B2 | 3/2016 | Poeze et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,392,945 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,474,474 | B2 | 10/2016 | Lamego et al. |
| 9,480,435 | B2 | 11/2016 | Olsen |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,560,996 | B2 | 2/2017 | Kiani |
| 9,579,039 | B2 | 2/2017 | Jansen et al. |
| 9,622,692 | B2 | 4/2017 | Lamego et al. |
| D788,312 | S | 5/2017 | Al-Ali et al. |
| 9,649,054 | B2 | 5/2017 | Lamego et al. |
| 9,697,928 | B2 | 7/2017 | Al-Ali et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,749,232 | B2 | 8/2017 | Sampath et al. |
| 9,750,442 | B2 | 9/2017 | Olsen |
| 9,750,461 | B1 | 9/2017 | Telfort |
| 9,775,545 | B2 | 10/2017 | Al-Ali et al. |
| 9,778,079 | B1 | 10/2017 | Al-Ali et al. |
| 9,782,077 | B2 | 10/2017 | Lamego et al. |
| 9,787,568 | B2 | 10/2017 | Lamego et al. |
| 9,808,188 | B1 | 11/2017 | Perea et al. |
| 9,839,379 | B2 | 12/2017 | Al-Ali et al. |
| 9,839,381 | B1 | 12/2017 | Weber et al. |
| 9,847,749 | B2 | 12/2017 | Kiani et al. |
| 9,848,800 | B1 | 12/2017 | Lee et al. |
| 9,861,298 | B2 | 1/2018 | Eckerbom et al. |
| 9,861,305 | B1 | 1/2018 | Weber et al. |
| 9,877,650 | B2 | 1/2018 | Muhsin et al. |
| 9,891,079 | B2 | 2/2018 | Dalvi |
| 9,924,897 | B1 | 3/2018 | Abdul-Hafiz |

(56)     References Cited

U.S. PATENT DOCUMENTS

| | | | |
|---|---|---|---|
| 9,936,917 | B2 | 4/2018 | Poeze et al. |
| 9,955,937 | B2 | 5/2018 | Telfort |
| 9,965,946 | B2 | 5/2018 | Al-Ali et al. |
| D820,865 | S | 6/2018 | Muhsin et al. |
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,086,138 | B1 | 10/2018 | Novak, Jr. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,205,291 | B2 | 2/2019 | Scruggs et al. |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| RE47,353 | E | 4/2019 | Kiani et al. |
| 10,279,247 | B2 | 5/2019 | Kiani |
| 10,292,664 | B2 | 5/2019 | Al-Ali |
| 10,299,720 | B2 | 5/2019 | Brown et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,966,655 | B2 | 4/2021 | Chen et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |

(56)                 References Cited

U.S. PATENT DOCUMENTS

| | | |
|---|---|---|
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| D1,060,680 S | 2/2025 | Al-Ali et al. |
| D1,061,585 S | 2/2025 | Indorf |
| D1,063,893 S | 2/2025 | DeJong et al. |
| 12,220,207 B2 | 2/2025 | Telfort et al. |
| 12,235,941 B2 | 2/2025 | Kiani et al. |
| 12,236,767 B2 | 2/2025 | Muhsin |
| D1,066,244 S | 3/2025 | Lim et al. |
| D1,066,672 S | 3/2025 | Al-Ali et al. |
| D1,068,656 S | 4/2025 | Trevisan et al. |
| D1,071,195 S | 4/2025 | Seung |
| D1,072,836 S | 4/2025 | Indorf |
| D1,072,837 S | 4/2025 | Ahmed et al. |
| 12,272,445 B1 | 4/2025 | Kiani |
| D1,078,689 S | 6/2025 | Hwang |
| D1,079,020 S | 6/2025 | Hwang |
| 12,336,796 B2 | 6/2025 | Al-Ali |
| D1,083,653 S | 7/2025 | DeJong et al. |
| D1,085,102 S | 7/2025 | Indorf et al. |
| 12,362,596 B2 | 7/2025 | Barker et al. |
| 12,390,114 B2 | 8/2025 | Novak, Jr. et al. |
| D1,092,244 S | 9/2025 | DeJong et al. |
| D1,093,406 S | 9/2025 | Indorf et al. |
| D1,094,735 S | 9/2025 | DeJong et al. |
| D1,095,288 S | 9/2025 | Lim |
| D1,095,483 S | 9/2025 | DeJong et al. |
| 12,433,524 B2 | 10/2025 | Al-Ali et al. |
| 12,440,128 B2 | 10/2025 | Al-Ali et al. |
| D1,102,622 S | 11/2025 | Al-Ali et al. |
| 12,478,272 B2 | 11/2025 | Telfort et al. |
| 12,478,293 B1 | 11/2025 | Al-Ali et al. |
| D1,106,466 S | 12/2025 | Avendaño et al. |
| 12,495,967 B2 | 12/2025 | Muhsin et al. |
| 12,495,999 B2 | 12/2025 | Al-Ali et al. |
| 12,507,952 B2 | 12/2025 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0139667 A1* | 7/2003 | Hewko ............... A61B 5/0059 |
| | | 600/410 |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0216098 A1* | 8/2009 | Stranc .................. A61B 5/413 |
| | | 600/328 |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0109617 A1* | 4/2015 | Gilbert ............. A61B 5/14532 |
| | | 250/234 |
| 2016/0120468 A1 | 5/2016 | Mathew et al. |
| 2017/0024748 A1 | 1/2017 | Haider |
| 2017/0251974 A1 | 9/2017 | Shreim et al. |

(56) References Cited

U.S. PATENT DOCUMENTS

| | | | |
|---|---|---|---|
| 2018/0242926 A1 | 8/2018 | Muhsin et al. |
| 2018/0247712 A1 | 8/2018 | Muhsin et al. |
| 2019/0320906 A1 | 10/2019 | Olsen |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329983 A1 | 10/2020 | Al-Ali et al. |
| 2020/0329993 A1 | 10/2020 | Al-Ali et al. |
| 2020/0367816 A1* | 11/2020 | Panneer Selvam .. A61B 5/7475 |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236003 A1 | 8/2021 | LeBoeuf et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |
| 2021/0290120 A1 | 9/2021 | Ai-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |
| 2025/0100482 A1 | 3/2025 | Al-Ali et al. |
| 2025/0118415 A1 | 4/2025 | Olsen |
| 2025/0255764 A1 | 8/2025 | Stead |
| 2025/0278512 A1 | 9/2025 | Koo et al. |
| 2025/0281059 A1 | 9/2025 | Avendano |
| 2025/0288250 A1 | 9/2025 | Al-Ali et al. |
| 2025/0295366 A1 | 9/2025 | Al-Ali et al. |
| 2025/0302426 A1 | 10/2025 | Ha et al. |
| 2025/0311949 A1 | 10/2025 | Al-Ali et al. |
| 2025/0318761 A1 | 10/2025 | Al-Ali et al. |
| 2025/0322950 A1 | 10/2025 | Al-Ali et al. |
| 2025/0323417 A1 | 10/2025 | Rey |
| 2025/0329240 A1 | 10/2025 | Kiani |
| 2025/0344010 A1 | 11/2025 | Al-Ali et al. |

OTHER PUBLICATIONS

International Search Report and Written Opinion received in PCT Application No. PCT/US2023/067017 dated Sep. 20, 2023 in 12 pages.

* cited by examiner emitters detectors

140

121

122

120

HYDRATION MEASUREMENT USING OPTICAL SENSORS

CROSS REFERENCE TO RELATED APPLICATIONS

This application claims benefit of priority and is related to U.S. Provisional Patent Application No. 63/364,866, filed May 17, 2022 and U.S. Provisional Patent Application No. 63/373,987, filed Aug. 30, 2022. The disclosures of each of the aforementioned applications are incorporated herein in their entireties for all purposes. Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to a systems, devices, and methods for monitoring a user's hydration.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\varepsilon_{i,\lambda}$ at a particular wavelength $\lambda$.

In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \Sigma_{i=1}^{n} \varepsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve equations 1 and 2 is the number of significant absorbers that are present in the solution.

A practical application of this technique is pulse oximetry or plethysmography, which utilizes a noninvasive sensor to measure oxygen saturation and pulse rate, among other physiological parameters. Pulse oximetry or plethysmography relies on a sensor attached externally to the patient (typically for example, at the fingertip, foot, ear, forehead, or other measurement sites) to output signals indicative of various physiological parameters, such as a patient's blood constituents and/or analytes, including for example a percent value for arterial oxygen saturation, among other physiological parameters. The sensor has at least one emitter that transmits optical radiation of one or more wavelengths into a tissue site and at least one detector that responds to the intensity of the optical radiation (which can be reflected from or transmitted through the tissue site) after absorption by pulsatile arterial blood flowing within the tissue site. Based upon this response, a processor determines the relative concentrations of oxygenated hemoglobin (HbO$_2$) and deoxygenated hemoglobin (Hb) in the blood so as to derive oxygen saturation, which can provide early detection of potentially hazardous decreases in a patient's oxygen supply, and other physiological parameters.

A patient monitoring device can include a plethysmograph sensor. The plethysmograph sensor can calculate oxygen saturation (SpO$_2$), pulse rate, a plethysmograph waveform, perfusion index (PI), pleth variability index (PVI), methemoglobin (MetHb), carboxyhemoglobin (CoHb), total hemoglobin (tHb), respiration rate, glucose, and/or otherwise. The parameters measured by the plethysmograph sensor can display on one or more monitors the foregoing parameters individually, in groups, in trends, as combinations, or as an overall wellness or other index.

A pulse oximetry sensor is described in U.S. Pat. No. 6,088,607 entitled Low Noise Optical Probe; pulse oximetry signal processing is described in U.S. Pat. Nos. 6,650,917 and 6,699,194 entitled Signal Processing Apparatus and Signal Processing Apparatus and Method, respectively; a pulse oximeter monitor is described in U.S. Pat. No. 6,584,336 entitled Universal Upgrading Pulse Oximeter; a wearable device including a pulse oximetry sensor is described in U.S. Patent Publication No. 2023/0028745 A1 entitled Wearable Device With Physiological Parameters Monitoring; all of which are assigned to Masimo Corporation, Irvine, CA, and each is incorporated by reference herein in its entirety.

Water content of tissue is also an informative diagnostic parameter. Dehydration may decrease cognitive and physical capabilities. Excessive hydration, on the other hand, may be symptomatic of any one of several clinically relevant conditions, such as cardiac, hepatic, or renal pathology; phlebitis; malnutrition and/or poor diet; allergies; food intolerance; pregnancy; abuse of laxatives, diuretics, and/or other drugs; use of contraceptives or hormone replacement therapy.

SUMMARY

Various implementations of systems, methods and devices within the scope of the appended claims each have several aspects, no single one of which is solely responsible for the desirable attributes described herein. Without limiting the scope of the appended claims, the description below describes some prominent features.

Details of one or more implementations of the subject matter described in this specification are set forth in the accompanying drawings and the description below. Other features, aspects, and advantages will become apparent from the description, the drawings, and the claims. Note that relative dimensions of the following figures may not be drawn to scale.

The devices, systems, and methods of the present disclosure each have several innovative aspects, no single one of which is solely responsible for its desirable attributes. Without limiting the scope of the present disclosure, its more prominent features will now be discussed briefly.

Monitoring tissue water content may be useful to indicate hydration status for persons undergoing physical activity, for example exercise. Low body hydration can cause health problems and may negatively affect athletic performance. Further, some pathologic symptoms caused by dehydration include problems with digestion, high blood pressure, cramping, and more.

Optical sensors can provide information relating to tissue constituents of a subject. Tissue constituents can include hemoglobin and water among other things. Optical sensors can employ radiation at a plurality of wavelengths. Each of the wavelengths may be more sensitive to absorption, attenuation, scattering, etc. by particular constituents of the tissue than other wavelengths. Various wavelengths may thus provide different information regarding various tissue constituents. The information corresponding to various wavelengths may facilitate determining a more accurate hydration estimation.

A physiological monitoring system can non-invasively monitor a subject's hydration in real-time using optical sensors. The physiological monitoring system can comprise a wearable device and one or more hardware computer processors. The wearable device can secure to a subject. The wearable device can comprise one or more optical emitters and one or more optical detectors. The one or more optical emitters can emit optical radiation toward a tissue of the subject. The optical radiation can include a water-dependent wavelength and a water-independent wavelength. The one or more optical detectors can detect the optical radiation emitted by the one or more optical detectors after attenuation through the tissue of the subject. The one or more optical detectors can generate optical data in response to detecting the optical radiation. The one or more hardware computer processors can access the optical data. The one or more hardware computer processors can determine a water-dependent optical parameter based on the optical data corresponding to the water-dependent wavelength. The one or more hardware computer processors can determine a water-independent optical parameter based on the optical data corresponding to the water-independent wavelength. The one or more hardware computer processors can determine a hydration index of the subject based on normalizing the water-dependent optical parameter with the water-independent optical parameter. The one or more hardware computer processors can generate user interface data for rendering an indication of the hydration index on a display.

In some implementations, the wearable device can further comprise a device display configured to render one or more user interfaces including physiological data of the subject. The one or more hardware computer processors can generate the user interface data for rendering the indication of the hydration index on the device display.

In some implementations, normalizing the water-dependent optical parameter with the water-independent optical parameter can include dividing the water-dependent optical parameter by the water-independent optical parameter.

In some implementations, normalizing the water-dependent optical parameter with the water-independent optical parameter includes subtracting the water-independent optical parameter from the water-dependent optical parameter.

In some implementations, the water-dependent optical parameter corresponds to an optical intensity of the water-dependent wavelength of the radiation detected by the one or more optical detectors, and the water-independent optical parameter corresponds to an optical intensity of the water-independent wavelength of the radiation detected by the one or more optical detectors.

In some implementations, the water-dependent optical parameter corresponds to an absorption of the water-dependent wavelength of the radiation by the tissue, and the water-independent optical parameter corresponds to an absorption of the water-independent wavelength of the radiation by the tissue.

In some implementations, the water-dependent wavelength of the radiation is sensitive to absorption by water, and absorption of the water-independent wavelength of the radiation is substantially unaffected by water.

In some implementations, the water-dependent wavelength of the radiation is greater than 700 nm.

In some implementations, the water-dependent wavelength of the radiation is greater than 800 nm.

In some implementations, the water-dependent wavelength of the radiation is greater than 900 nm.

In some implementations, the water-dependent wavelength of the radiation is between 900 nm and 1000 nm.

In some implementations, the water-dependent wavelength of the radiation is 970 nm.

In some implementations, the water-dependent wavelength of the radiation is 905 nm.

In some implementations, the water-independent wavelength of the radiation is less than 700 nm.

In some implementations, the water-independent wavelength of the radiation is between 600 nm and 700 nm.

In some implementations, wherein the water-independent wavelength of the radiation is 660 nm.

In some implementations, wherein the water-independent wavelength of the radiation is 620 nm.

In some implementations, the one or more hardware computer processors can adjust the optical data based on a wavelength associated with the optical data, and adjusting the optical data includes increasing a magnitude of the optical data associated with a wavelength to which a detector is less sensitive.

In some implementations, the one or more hardware computer processors can determine the hydration index based on calibration data including a calibration curve of empirical data.

In some implementations, the wearable device includes a watch.

In some implementations, the wearable device includes an auricular device.

In some implementations, the wearable device includes a finger sensor.

In some implementations, the wearable device is configured to secure to a wrist region of the subject.

In some implementations, the wearable device is configured to secure to a finger of the subject.

In some implementations, the wearable device is configured to secure to an ear of the subject.

In some implementations, the wearable device is configured to secure to a foot of the subject.

In some implementations, the wearable device is configured to secure to a head of the subject.

In some implementations, the wearable device further comprises the one or more hardware computer processors.

In some implementations, the one or more hardware computer processors are disposed within a computing device remote to the wearable device.

In some implementations, the computing device includes a phone.

In some implementations, the computing device includes a server.

In some implementations, the one or more hardware computer processors can determine a hydration protocol based on at least the hydration index, and the hydration protocol includes a recommended amount of fluid to hydrate.

In some implementations, the one or more hardware computer processors can determine a hydration protocol based on at least the hydration index, and the hydration protocol includes a recommended time to hydrate.

In some implementations, the one or more hardware computer processors can determine a hydration protocol based on at least the hydration index, and the hydration protocol includes a recommended time to exercise.

In some implementations, the one or more hardware computer processors can determine a hydration protocol based on at least the hydration index, and the hydration protocol includes an estimated time to dehydration.

In some implementations, the one or more hardware computer processors can access reference optical data corresponding to other radiation attenuated through a reference medium. The other radiation can include the water-dependent wavelength and water-independent wavelength. The one or more hardware computer processors can determine the water-dependent optical parameter based on normalizing the optical data corresponding to the water-dependent wavelength with the reference optical data corresponding to the water-dependent wavelength. The one or more hardware computer processors can determine the water-independent optical parameter based on normalizing the optical data corresponding to the water-independent wavelength with the reference optical data corresponding to the water-independent wavelength.

In some implementations, the optical data corresponds to an optical density of the tissue, and the reference optical data corresponds to an optical density of the reference medium.

In some implementations, the reference medium is air.

In some implementations, normalizing the optical data with the reference optical data includes dividing the optical data by the reference optical data.

In some implementations, the one or more hardware computer processors can determine a second water-dependent optical parameter based on a second water-dependent wavelength of the radiation. The one or more hardware computer processors can determine a second water-independent optical parameter based on a second water-independent wavelength of the radiation. The one or more hardware computer processors can determine the hydration index based on normalizing a difference between the water-dependent optical parameter and the second water-dependent optical parameter with a difference between the water-independent optical parameter and the second water-independent optical parameter.

In some implementations, the second water-dependent wavelength of the radiation is greater than 800 nm.

In some implementations, the second water-dependent wavelength of the radiation is between 900 nm and 1000 nm.

In some implementations, the water-dependent wavelength of the radiation is 970 nm, and the second water-dependent wavelength of the radiation is 905 nm.

In some implementations, the second water-independent wavelength of the radiation is less than 700 nm.

In some implementations, the second water-independent wavelength of the radiation is between 600 nm and 700 nm.

In some implementations, the water-independent wavelength of the radiation is 620 nm, and wherein the second water-independent wavelength of the radiation is 660 nm.

In some implementations, the water-dependent optical parameter corresponds to an estimated area integrated under an absorption curve between the water-dependent wavelength and the second water-dependent wavelength.

In some implementations, the water-independent optical parameter corresponds to an estimated area integrated under an absorption curve between the water-independent wavelength and the second water-independent wavelength.

In some implementations, the one or more hardware computer processors can access reference optical data corresponding to other radiation attenuated through a reference medium, wherein the other radiation includes the water-dependent wavelength, a second water-dependent wavelength, the water-independent wavelength, and a second water-independent wavelength, wherein the radiation includes the second water-dependent wavelength and the second water-independent wavelength. The one or more hardware computer processors can determine the water-dependent optical parameter based on normalizing the optical data corresponding to the water-dependent wavelength with the reference optical data corresponding to the water-dependent wavelength. The one or more hardware computer processors can determine a second water-dependent optical parameter based on normalizing the optical data corresponding to the second water-dependent wavelength with the reference optical data corresponding to the second water-dependent wavelength. The one or more hardware computer processors can determine the water-independent optical parameter based on normalizing the optical data corresponding to the water-independent wavelength with the reference optical data corresponding to the water-independent wavelength. The one or more hardware computer processors can determine a second water-independent optical parameter based on normalizing the optical data corresponding to the second water-independent wavelength with the reference optical data corresponding to the second water-independent wavelength. The one or more hardware computer processors can determine the hydration index of the tissue based on normalizing a difference between the water-dependent optical parameter and the second water-dependent optical parameter with a difference between the water-independent optical parameter and the second water-independent optical parameter.

In some implementations, the second water-dependent wavelength of the radiation is between 900 nm and 1000 nm, and the second water-independent wavelength of the radiation is between 600 nm and 700 nm.

In some implementations, the water-dependent wavelength of the radiation is 970 nm, the second water-dependent wavelength of the radiation is 905 nm, the water-independent wavelength of the radiation is 620 nm, and the second water-independent wavelength of the radiation is 660 nm.

A method of non-invasively monitoring a subject's hydration in real-time using optical sensors can comprise emitting, by one or more optical emitters, optical radiation toward a tissue of a subject. The optical radiation includes a water-dependent wavelength and a water-independent wavelength. The method can further comprise detecting, by one or more optical detectors, the optical radiation emitted after attenuation through the tissue of the subject. The method can further comprise generating optical data in response to detecting the optical radiation. The method can further comprise determining a water-dependent optical parameter based on the optical data corresponding to the water-dependent wavelength. The method can further comprise determining a water-independent optical parameter based on the optical data corresponding to the water-independent wavelength. The method can further comprise determining a hydration index of the subject based on normalizing the water-dependent optical parameter with the water-independent optical parameter. The method can further comprise generating user interface data for rendering an indication of the hydration index on a display. The method can further comprise displaying, via the display, the indication of the hydration index.

Non-transitory computer-readable media can include computer-executable instructions that, when executed by a computing system, cause the computing system to perform operations comprising emitting, by one or more optical emitters, optical radiation toward a tissue of a subject, wherein the optical radiation includes a water-dependent wavelength and a water-independent wavelength; detecting, by one or more optical detectors, the optical radiation emitted after attenuation through the tissue of the subject; generating optical data in response to detecting the optical radiation; determining a water-dependent optical parameter based on the optical data corresponding to the water-dependent wavelength; determining a water-independent optical parameter based on the optical data corresponding to the water-independent wavelength; determining a hydration index of the subject based on normalizing the water-dependent optical parameter with the water-independent optical parameter; generating user interface data for rendering an indication of the hydration index on a display; and displaying, via the display, the indication of the hydration index.

A physiological monitoring system can non-invasively monitor a subject's hydration in real-time using optical sensors. The physiological monitoring system can comprise a wearable device configured to secure to a subject and one or more hardware computer processors. The wearable device can comprise one or more optical emitters and one or more optical detectors. The one or more optical emitters can emit optical radiation toward a tissue of the subject. The optical radiation can include a water-dependent wavelength between 900 nm and 1000 nm. The optical radiation can include a water-independent wavelength between 600 nm and 700 nm. The one or more optical detectors can detect the optical radiation emitted by the one or more optical detectors after attenuation through the tissue of the subject; and generate optical data in response to detecting the optical radiation. The one or more hardware computer processors can access the optical data; determine a water-dependent optical parameter based on the optical data corresponding to the water-dependent wavelength; determine a water-independent optical parameter based on the optical data corresponding to the water-independent wavelength; determine a hydration index of the subject based on the water-dependent optical parameter and the water-independent optical parameter; and generate user interface data for rendering an indication of the hydration index on a display.

In some implementations, the wearable device can further comprise a device display configured to render one or more user interfaces including physiological data of the subject. The one or more hardware computer processors can generate the user interface data for rendering the indication of the hydration index on the device display.

A physiological monitoring system for monitoring a subject's hydration using optical sensors can comprise one or more optical emitters, one or more optical detectors, and one or more hardware computer processors. The one or more optical emitters can emit optical radiation toward a tissue of the subject. The optical radiation can include a water-dependent wavelength between 900 nm and 1000 nm. The optical radiation can include a water-independent wavelength between 600 nm and 700 nm. The one or more optical detectors can detect the optical radiation emitted by the one or more optical detectors after attenuation through the tissue of the subject. The one or more optical detectors can generate optical data in response to detecting the optical radiation. The one or more hardware computer processors can access the optical data. The one or more hardware computer processors can determine a hydration index of the subject based on the optical data corresponding to the water-dependent wavelength and the water-independent wavelength.

A physiological monitoring system for non-invasively monitoring a subject's hydration using optical sensors can comprise one or more optical emitters, one or more optical detectors, and one or more hardware computer processors.

The one or more optical emitters can emit optical radiation toward a tissue of a subject. The optical radiation can include a plurality of water-dependent wavelengths and a plurality of water-independent wavelengths. The one or more optical detectors can detect the optical radiation emitted by the one or more optical detectors after attenuation through the tissue of the subject. The one or more optical detectors can generate optical data in response to detecting the optical radiation. The one or more hardware computer processors can access the optical data; and determine a hydration index of the subject based on normalizing the optical data corresponding to the plurality of water-dependent wavelengths with the optical data corresponding to the plurality of water-independent wavelengths.

In some implementations, each of the wavelengths of the plurality of water-dependent wavelengths is greater than 800 nm.

In some implementations, each of the wavelengths of the plurality of water-dependent wavelengths is between 900 nm and 1000 nm.

In some implementations, the plurality of water-dependent wavelengths includes at least a first wavelength of 905 nm and a second wavelength of 970 nm.

In some implementations, the plurality of water-dependent wavelengths includes at least two wavelengths.

In some implementations, each of the wavelengths of the plurality of water-independent wavelengths is less than 700 nm.

In some implementations, each of the wavelengths of the plurality of water-independent wavelengths is between 600 nm and 700 nm.

In some implementations, the plurality of water-independent wavelengths includes at least a first wavelength of 620 nm and a second wavelength of 660 nm.

In some implementations, the plurality of water-independent wavelengths includes at least two wavelengths.

A physiological monitoring system for non-invasively monitoring a subject's hydration using optical sensors can comprise one or more optical emitters, one or more optical detectors, and one or more hardware computer processors. The one or more optical emitters can emit optical radiation toward a tissue of a subject. The optical radiation can include a plurality of water-dependent wavelengths and a plurality of water-independent wavelengths. The one or more optical detectors can detect the optical radiation emitted by the one or more optical detectors after attenuation through the tissue of the subject. The one or more optical detectors can generate optical data in response to detecting the optical radiation. The one or more hardware computer processors can access the optical data. The one or more hardware computer processors can determine a water-dependent optical parameter based on the optical data corresponding to the plurality of water-dependent wavelengths. The water-dependent optical parameter can correspond to at least a portion of an estimated area under a water absorption curve between the plurality of water-dependent wavelengths. The one or more hardware computer processors can determine a water-independent optical parameter based on the optical data corresponding to the plurality of water-independent wavelengths. The water-independent optical parameter can correspond to at least a portion of an estimated area under a hemoglobin absorption curve between the plurality of water-independent wavelengths. The one or more hardware computer processors can determine a hydration index of the subject based on the water-dependent optical parameter and the water-independent optical parameter.

In some implementations, the hemoglobin absorption curve includes an oxy-hemoglobin absorption curve.

In some implementations, the hemoglobin absorption curve includes a deoxy-hemoglobin absorption curve.

A physiological monitoring system for non-invasively monitoring a subject's hydration can comprise one or more hardware computer processors. The one or more hardware computer processors can execute a plurality of computer executable instructions to cause the physiological monitoring system to access optical data corresponding to radiation attenuated through a medium and detected at a detector. The one or more hardware computer processors can execute a plurality of computer executable instructions to cause the physiological monitoring system to determine a water-dependent optical parameter based on a water-dependent wavelength of the radiation. The one or more hardware computer processors can execute a plurality of computer executable instructions to cause the physiological monitoring system to determine a water-independent optical parameter based on a water-independent wavelength of the radiation. The one or more hardware computer processors can execute a plurality of computer executable instructions to cause the physiological monitoring system to determine a hydration index of the medium based on normalizing the water-dependent optical parameter with the water-independent optical parameter.

A computer-implemented method can comprise accessing optical data corresponding to radiation attenuated through a medium and detected at a detector. The computer-implemented method can comprise determining a water-dependent optical parameter based on a water-dependent wavelength of the radiation. The computer-implemented method can comprise determining a water-independent optical parameter based on a water-independent wavelength of the radiation. The computer-implemented method can comprise determining a hydration index of the medium based on normalizing the water-dependent optical parameter with the water-independent optical parameter.

A computing system can comprise one or more hardware computer processors. The one or more hardware computer processors can execute a plurality of computer executable instructions to cause the computing system to access first optical data corresponding to a water-dependent radiation wavelength attenuated through a medium and detected at a detector. The one or more hardware computer processors can execute a plurality of computer executable instructions to cause the computing system to access second optical data corresponding to a water-independent radiation wavelength attenuated through the medium and detected at the detector. The one or more hardware computer processors can execute a plurality of computer executable instructions to cause the computing system to determine a hydration index of the medium based on the first and second optical data.

A physiological monitoring system for monitoring a subject's hydration using optical sensors can comprise one or more optical emitters, one or more optical detectors, and one or more hardware computer processors. The one or more optical emitters can emit optical radiation toward a tissue of the subject. The optical radiation can include a water-dependent wavelength and a water-independent wavelength. The one or more optical detectors can detect the optical radiation emitted by the one or more optical detectors after attenuation through the tissue of the subject. The one or more optical detectors can generate optical data in response to detecting the optical radiation. The one or more hardware computer processors can access the optical data. The one or more hardware computer processors can determine a hydration index of the subject based on the optical data corresponding to the water-dependent wavelength and the water-independent wavelength. The one or more hardware computer processors can determine a hydration protocol for the subject based on at least the hydration index. The one or more hardware computer processors can generate user interface data for rendering an indication of the hydration protocol on a display.

In some implementations, the hydration protocol includes a recommended amount of fluid for the subject to consume.

In some implementations, the hydration protocol includes a recommended time for the subject to consume fluid.

In some implementations, the hydration protocol includes a recommended time to exercise.

In some implementations, the one or more hardware computer processors can generate one or more alerts based on the hydration protocol.

In some implementations, the one or more hardware computer processors can generate one or more alerts based on the hydration index.

In some implementations, the physiological monitoring system further comprises a wearable device. The wearable device can comprise a device display. The one or more hardware computer processors can generate the user interface data for rendering the indication of the hydration protocol on the device display.

This disclosure provides methods, systems, and/or devices capable of detecting a subject's hydration by optical sensing. A physiological monitoring system can include a hardware processor. A physiological monitoring system can include a device including an optical sensor configured to collect physiological data from a subject. The device may be remote to the hardware processor. The device may be portable. The device may include a wearable device. The device may secure to a subject. The device may adhere to a subject. The device may be a watch. The device may be an adhesive patch. The adhesive patch may include electronics. The device may be a phone. The device may be an earbud. The device may collect physiological data from a body portion of a subject, such as but not limited to, a head, forehead, face, ears, nose, neck, shoulders, arms, forearms, hands, fingers, digits, stomach, back, chest, torso, abdomen, hips, legs, thighs, calves, ankle, feet toes, etc. The device may be incorporated as part of clothing, such as a hat, shirt, pants, shorts, socks, booties, shoes, sweatband, armband, headband, glove, or other article of apparel donned by a subject.

In certain aspects, the present disclosure provides a method of estimating a user's hydration, including: transmitting light of a first wavelength, a second wavelength, a third wavelength, and a fourth wavelength to the skin of a user; measuring a first absorption of the user's tissue corresponding to the first wavelength, a second absorption of the user's tissue corresponding to the second wavelength, a third absorption of the user's tissue corresponding to the third wavelength, and a fourth absorption of the user's tissue corresponding to the fourth wavelength; integrating across the first absorption and the second absorption to generate a first hydration parameter; integrating across the third absorption and the fourth absorption to generate a second hydration parameter; comparing the second hydration parameter to the first hydration parameter to generate a result.

In some implementations, the tissue absorption of the first wavelength and second wavelength may not be substantially affected by the user's hydration. In some implementations, the tissue absorption of the third wavelength and fourth wavelength may be substantially affected by the user's hydration. In some implementations, the method may also include integrating the first absorption and the second absorption may include averaging the first absorption and second absorption and multiplying by the difference of the first wavelength and second wavelength. In some implementations, the method may also include integrating the third absorption and the fourth absorption comprising averaging the third absorption and fourth absorption and multiplying by the difference of the third wavelength and fourth wavelength. In some implementations, the method may also include projecting the first absorption and second absorptions to their respective values at 95% $SpO_2$, if the user's $SpO_2$ is less than 95%. In some implementations, the method may also include transmitting light of a fifth wavelength to the user's skin, wherein the fifth wavelength may be between the first wavelength and second wavelength; measuring a fifth absorption of the user's tissue corresponding to the fifth wavelength; and integrating across the first absorption, fifth absorption, and second absorption to generate the first hydration parameter. In some implementations, the method may also include transmitting light of a fifth wavelength to the user's skin, wherein the fifth wavelength may be between the third wavelength and fourth wavelength; measuring a fifth absorption of the user's tissue corresponding to the fifth wavelength; and integrating across the third absorption, fifth absorption, and fourth absorption to generate the second hydration parameter. In some implementations, the first wavelength may be within a range of about 400 nm to 660 nm. The first wavelength may be within a range of about 610 nm to 630 nm. The first wavelength may be about 620 nm. In some implementations, the second wavelength may be within a range of about 620 nm to 700 nm. The second wavelength may be within a range of about 650 nm to 670 nm. The second wavelength may be about 660 nm. In some implementations, the third wavelength may be within a range of about 800 nm to 970 nm. The third wavelength may be within a range of about 895 nm to 915 nm. The third wavelength may be about 905 nm. In some implementations, the fourth wavelength may be within a range of about 905 nm to 1400 nm. The fourth wavelength may be within a range of about 960 nm to 980 nm. The fourth wavelength may be about 970 nm.

In certain aspects, the present disclosure provides a method of estimating a user's hydration, including: integrating across a first pair of tissue absorbances to generate a first hydration parameter; integrating across a second pair of tissue absorbances to generate a second hydration parameter; comparing the first hydration parameter and the second hydration parameter.

In certain aspects, the present disclosure provides a system capable of estimating a user's hydration including: one or more light sources configured to emit light at a first wavelength, at a second wavelength, at a third wavelength, and at a fourth wavelength; an optical sensor configured to measure a first tissue absorbance corresponding to the first wavelength, a second tissue absorbance corresponding to the second wavelength, a third tissue absorbance corresponding to the third wavelength, and a fourth tissue absorbance corresponding to the fourth wavelength; a processor configured to receive the first, second, third, and fourth tissue absorbances, integrate the first tissue absorbance and the second tissue absorbance to generate a first hydration parameter, integrate the third tissue absorbance and fourth tissue absorbance to generate a second hydration parameter, and compare the first hydration parameter and second hydration parameter to generate a result.

In some implementations, the system may include a first light source configured to emit light at the first wavelength, a second light source configured to emit light at the second wavelength, a third light source configured to emit light at the third wavelength, a fourth light source configured to emit light at the fourth wavelength. In some implementations, each of the first wavelength, second wavelength, third wavelength, and fourth wavelength may be different. In some implementations, tissue absorption of the first wavelength and second wavelength may not be substantially affected by the user's hydration. In some implementations, tissue absorption of the third wavelength and fourth wavelength may be substantially affected by the user's hydration. In some implementations, the first wavelength may be within a range of about 400 nm to 660 nm. The first wavelength may be within a range of about 610 nm to 630 nm. The first wavelength may be about 620 nm. In some implementations, the second wavelength may be within a range of about 620 nm to 700 nm. The second wavelength may be within a range of about 650 nm to 670 nm. The second wavelength may be about 660 nm. In some implementations, the third wavelength may be within a range of about 800 nm to 970 nm. The third wavelength may be within a range of about 895 nm to 915 nm. The third wavelength may be about 905 nm. In some implementations, the fourth wavelength may be within a range of about 905 nm to 1400 nm. The fourth wavelength may be within a range of about 960 nm to 980 nm. The fourth wavelength may be about 970 nm. In some implementations, the system may include a display configured to show the result. In some implementations, the system of may include a display configured to show the hydration level of the user. In some implementations, the system may be included in a wearable device.

BRIEF DESCRIPTION OF THE DRAWINGS

Various implementations will be described hereinafter with reference to the accompanying drawings. These implementations are illustrated and described by example only, and are not intended to limit the scope of the disclosure. In the drawings, similar elements may have similar reference numerals.

DETAILED DESCRIPTION

Figure 1A:
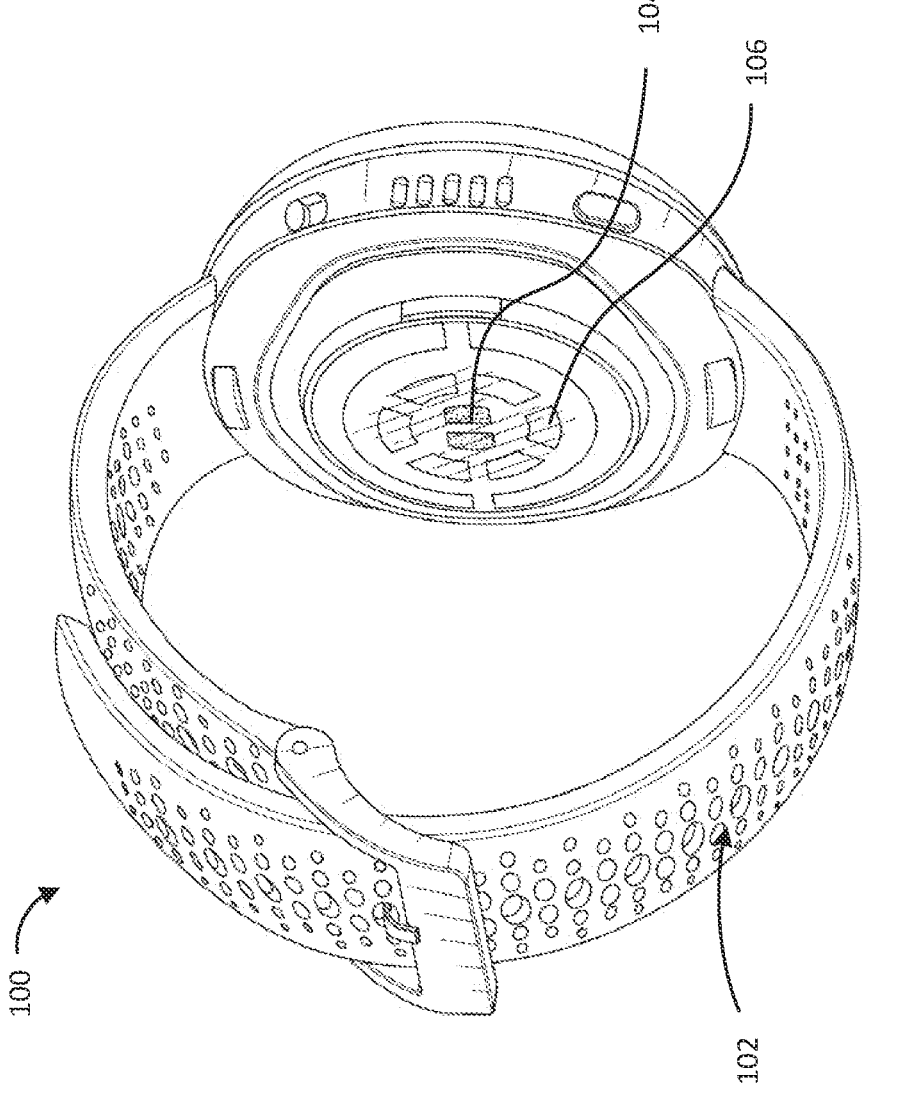
FIGS. 1A-1G illustrate example devices for measuring hydration of a subject.

The present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, the devices, systems, and/or methods disclosed herein can include several novel features, no single one of which is solely responsible for its desirable attributes or which is essential to practicing the devices, systems, and/or methods disclosed herein.

Although certain implementations and examples are described below, those of skill in the art will appreciate that the disclosure extends beyond the specifically disclosed implementations and/or uses and obvious modifications and equivalents thereof based on the disclosure herein. Thus, the scope of the disclosure herein should not be limited by any particular implementation and/or example described below.

A subject's hydration level may be assessed by measuring impedance and/or conductance to assess concentration of electrolytes in perspiration, which may be indicative of hydration levels. Alternatively, changes in a body's electrical impedance may be used to monitor changes in hydration. However, impedance and/or conductance may depend, in part, on anthropometric features of the subject, such as weight, age, gender, race, shoulder width, girth, waist-to-hip ratio, and body mass index. Further, impedance and conductance depend in part on the subject's electrolyte levels, which may vary independently of hydration. A model incorporating impedance and/or conductance measurements to estimate hydration may not address these variables, resulting in inaccurate measurements.

Magnetic resonance imaging (MRI) may be used to assess hydration. But MRI requires bulky equipment that cannot be easily moved. Additionally, MRI equipment is expensive and requires operation by a skilled technician. Additionally, an MRI scan may take over an hour.

Another method for estimating hydration is the dilution method, which involves orally administering a dose of a tracer to the subject. Typically, two blood or urine samples are collected: one just before administration of the tracer and one after a sufficient length of time, usually several minutes to hours. Hydration is estimated by relating the dose of tracer to the dilution of tracer in the second sample. The dilution method is time-consuming and inconvenient to the subject.

The present disclosure provides devices, systems, and methods that are capable of accurately, portably, conveniently, quickly, and/or non-invasively optically measuring a subject's hydration. Optical attenuation or absorbance by a medium such as a subject's tissue may be measured at wavelengths that are substantially unaffected by tissue water content and/or are affected by tissue water content. These absorbances may be analyzed to generate a quantitative indication of the subject's hydration.

FIG. 1A is a perspective view of an example wearable device 100. The wearable device 100 can be a watch such as smartwatch. The wearable device 100 may perform one or more physiological related functions. The wearable device 100 may perform one or more non-physiological related functions. The wearable device 100 can track and indicate time, perform data communications, play audio sounds, or the like. The wearable device 100 can include a display configured to display information, such as physiological information, to a user.

The wearable device 100 can include one or more straps 102. The straps 102 may be adjustable and may removably secure the wearable device 100 to a portion of a subject such as a wrist. In some implementations, the wearable device 100 may be secured to other portions of the body such as an ear, finger, arm, leg, ankle, neck, etc. The wearable device 100 can include one or more sensors such as physiological sensors. The wearable device 100 can include an optical sensor.

The wearable device 100 can include one or more emitters 104. The emitter(s) 104 can include one or more light emitting diodes (LEDs). The emitter(s) 104 may emit optical radiation of various wavelengths such as light which may penetrate into a tissue of the user of the wearable device 100.

The wearable device 100 can include one or more detectors 106. The detector(s) 106 may form a ring around the emitter(s) 104. The detector(s) 106 may detect optical radiation such as light emitted by the emitter(s) 104. The detector(s) 106 may generate one or more signals based at least in part on the radiation detected that was emitted by the emitter(s) 104. The detector(s) 106 may generate data relating to spectroscopy. The detector(s) 106 may generate data relating to a hydration status of the user. The detector(s) 106 may generate data relating to blood oxygen saturation of a user of the wearable device 100. The light emitters and detectors can be configured in a reflective sensor configuration or in a transmissive sensor configuration. For example, different types of sensor configurations and measurement sites are discussed below by way of non-limiting examples.

The sensor(s) of the wearable device 100, such as the emitter(s) 104, and/or the detector(s) 106, may be located on a housing of the wearable device 100. In some implementations, one or more of the sensors of the wearable device 100 may be located on a portion of the wearable device 100 housing that is not readily accessible to user. For example, a user may not be able to access the one or more sensors with their fingers and/or the sensors may not be visible to the user when worn. For example, the sensors may be located on an underside portion of the wearable device 100 such that when the wearable device 100 is worn by a user, the wearable device 100 covers the sensors against the user, such as against a wrist area of the user. In various implementations, the emitter(s) 104 and the detector(s) 106 may be arranged about the user's tissue such that the detector(s) 106 may detect light transmitted through the user's tissue. In some implementations, the emitter(s) 104 and the detector(s) 106 may be arranged on opposite sides of the user's tissue, such as on opposite sides of a finger. In other implementations, the emitter(s) 104 and the detector(s) 106 may be located on the same side of the tissue, such as on a same side of a wrist.

Figure 1C:
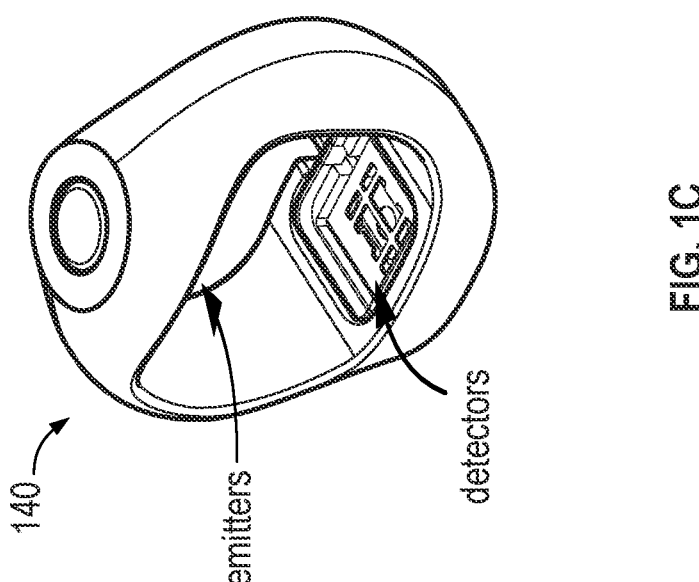
Figure 1B:
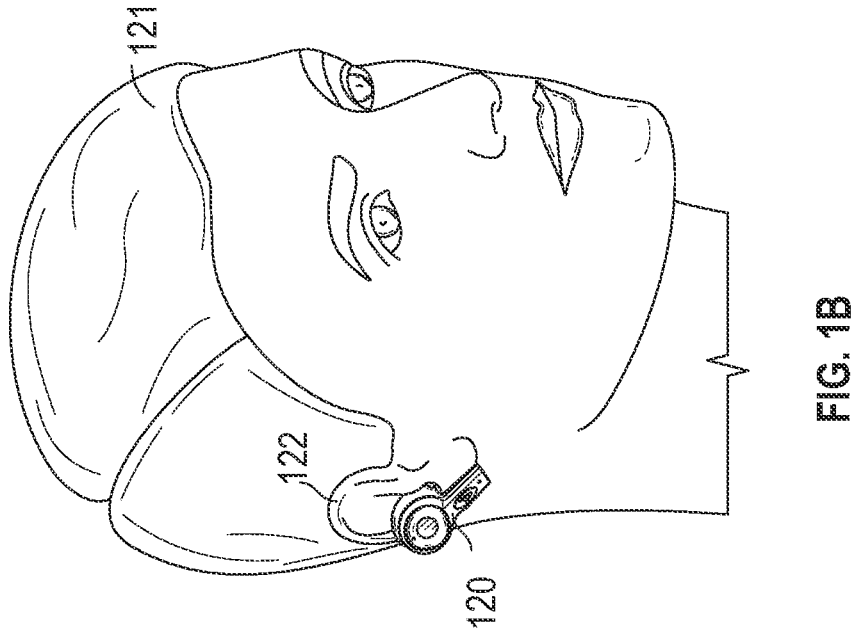

FIG. 1B illustrates another example wearable device 120. The wearable device 120 may be an auricular device. The wearable device 120 may be an earbud, earphone, headphone, or the like. The wearable device 120 may be secured to an ear 122 of a user 121. The wearable device 120 may be secured to a concha, pinna, tragus, anti-tragus, earlobe, etc. of the ear 122 of the user 121. The wearable device 120 may be positioned adjacent to an auditory canal of the user 121. The wearable device 120 may be positioned within an auditory canal of the user 121. A portion of the wearable device 120 may be positioned with an auditory canal of the user 121. An entirety of the wearable device 120 may be positioned with an auditory canal of the user 121. The wearable device 120 may emit audio signals such as music via speakers. The wearable device 120 may include one or more physiological sensors such as an optical sensor. The wearable device 120 can include optical emitters and optical detectors. An optical emitter of the wearable device 120 can emit optical radiation such as light into the ear 122 of the user 121 to collect physiological data of the user 121. An optical detector can detect radiation that has travelled through the ear 122 of the user 121. The wearable device 120 can include any of the structural and/or operational features shown and/or described as any of the other example wearable devices herein, such as wearable device 100.

FIG. 1C illustrates another example wearable device 140. The wearable device 140 may be secured to a digit of a user such as a finger, thumb, or toe. The wearable device 140 may be a ring. The wearable device 140 may include one or more physiological sensors such as an optical sensor. The wearable device 140 can include optical emitters and optical detectors. An optical emitter of the wearable device 140 can emit optical radiation such as light into a digit of a user to collect physiological data of the user. An optical detector can detect radiation that has travelled through the digit of the user. The wearable device 140 can include any of the structural and/or operational features shown and/or described as any of the other example wearable devices herein, such as wearable device 100.

Figure 1E:
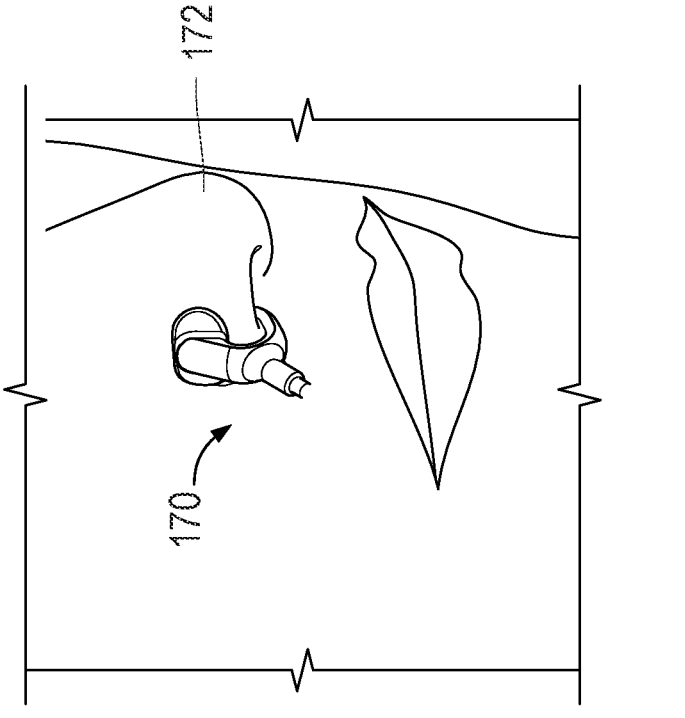
Figure 1D:
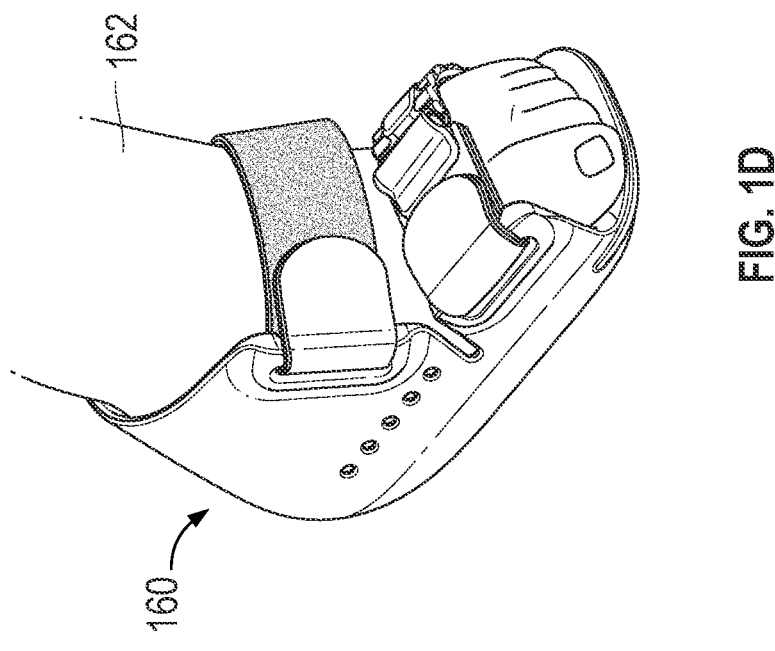

FIG. 1D illustrates another example a wearable device 160. The wearable device 160 may be secured to a foot 162 of a user, such as to a leg portion, an ankle portion, or the like. The wearable device 160 may include one or more physiological sensors such as an optical sensor. The wearable device 160 can include optical emitters and optical detectors. An optical emitter of the wearable device 160 can emit light into the foot 162 of the user to collect physiological data of the user. An optical detector can detect radiation that has travelled through the foot 162 of the user. The wearable device 160 can include any of the structural and/or operational features shown and/or described as any of the other example wearable devices herein, such as wearable device 100.

FIG. 1E illustrates another example a wearable device 170. The wearable device 170 may be secured to a nose 172 of a user. The wearable device 170 may be secured to a nostril, nasal bridge, etc. of the nose 172 of the user. The wearable device 170 may include one or more physiological sensors such as an optical sensor. The wearable device 170 can include optical emitters and optical detectors. An optical emitter of the wearable device 170 can emit light into the nose 172 of the user to collect physiological data of the user. An optical detector can detect radiation that has travelled through the nose 172 of the user. The wearable device 170 can include any of the structural and/or operational features shown and/or described as any of the other example wearable devices herein, such as wearable device 100.

Figure 1G:
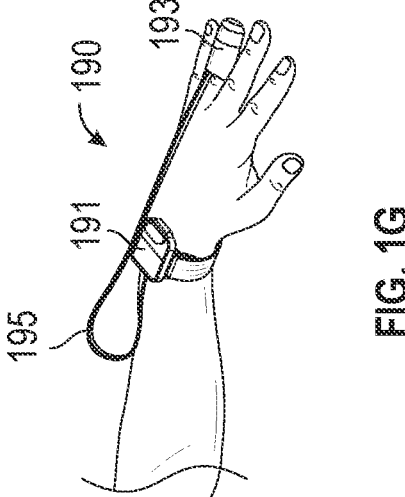
Figure 1F:
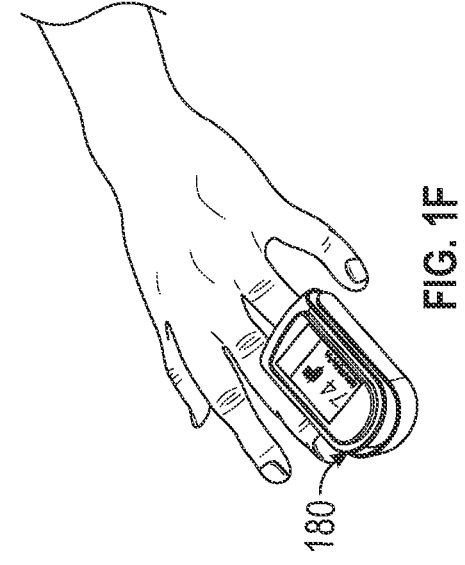

FIG. 1F illustrates another example a wearable device 180. The wearable device 180 may be secured to a digit of a subject such as a finger or a thumb. The wearable device 180 may include one or more physiological sensors such as an optical sensor. The wearable device 180 can include optical emitters and optical detectors. An optical emitter of the wearable device 180 can emit light into the digit of the subject to collect physiological data of the subject. An optical detector can detect radiation that has travelled through the digit of the subject. The wearable device 180 can include any of the structural and/or operational features shown and/or described as any of the other example wearable devices herein, such as wearable device 100.

FIG. 1G illustrates another example a wearable device 190. The wearable device 190 can include a sensor portion 193 and a control portion 191. The sensor portion 193 may be displaced from the control portion 191. The sensor portion 193 may be remote to the control portion 191. The sensor portion 193 may be connected with the control portion 191 via one or more cables 195. In some implementations, the sensor portion 193 may be wirelessly connected with the control portion 191. The control portion 191 can include a display. The control portion 191 may display physiological data of the subject. The wearable device 190 may be secured to a subject, such as to the subject's arm, forearm, wrist, hand, digit, finger, thumb, or the like. The control portion 191 may be secured to a wrist portion of a subject. The sensor portion 193 may be secured to a digit of the subject such as to a finger or thumb. The sensor portion 193 may include one or more physiological sensors such as an optical sensor. The sensor portion 193 can include optical emitters and optical detectors. An optical emitter of the sensor portion 193 can emit light into the digit of the subject to collect physiological data of the subject. An optical detector can detect radiation that has travelled through the digit of the subject. The wearable device 190 can include any of the structural and/or operational features shown and/or described as any of the other example wearable devices herein, such as wearable device 100.

FIGS. 1A-1G are provided as examples and are not intended to be limiting. Various wearable devices may be implemented which can affix to various portions of a user's body. In some implementations, a wearable device may be a headband, hat, helmet, glasses, or the like and may attach to a head portion of a user. In some implementations, a wearable device may be a wristband, armband, glove, or the like and may attach to an arm or hand portion of a user. In some implementations, a wearable device may be a necklace or the like and may attach to a neck portion of a user. In some implementations, a wearable device may be attached to a portion of a body that is different than the portion of the body from which it collects physiological data. For example, a wearable device may be worn around a neck of a user and may collect physiological data from a hand of a user. In some implementations, a wearable device can be secured to a user via one or more of adhesion, straps, friction force, elastic force, spring force, etc.

Figure 2:
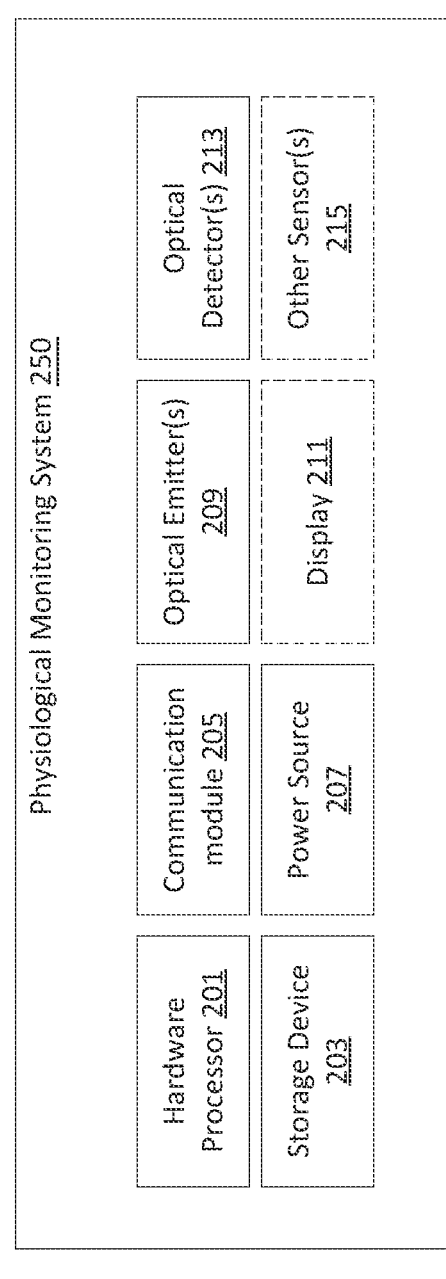
FIG. 2 is a block diagram illustrating an example implementation of a physiological monitoring system for measuring hydration of a subject.

FIG. 2 is a block diagram illustrating an example implementation of a physiological monitoring system 250. The physiological monitoring system 250 can include a hardware processor 201, a storage device 203, a communication module 205, a power source 207, one or more optical emitters 209, one or more optical detectors 213. The physiological monitoring system 250 can optionally include a display 211 and one or more other sensors 215. In some implementations, the physiological monitoring system 250 may include less than all of the components shown in FIG. 2.

In some implementations, one or more components of the physiological monitoring system 250 may be implemented on a wearable device, such as any of the example wearables devices shown and/or described herein, such as with reference to FIGS. 1A-1E. For example, wearable device 100 may comprise one or more components of the physiological monitoring system 250 within a housing of the wearable device 100. In some implementations, the physiological monitoring system 250 may be implemented as a single integrated unit such as within a same device. In some implementations, one or more components of the physiological monitoring system 250 may be implemented on separate devices. For example, the optical emitter(s) 209 and/or optical detector(s) 213 may be implemented on a wearable device and the hardware processor 201 may be implemented remote to the wearable device such as on a remote server or remote computing device.

The hardware processor 201 can be configured to execute program instructions to cause the physiological monitoring system 250 to perform one or more operations. The hardware processor 201 can be configured, among other things, to process data, execute instructions to perform one or more functions, and/or control the operation of the physiological monitoring system 250 or components thereof. For example, the hardware processor 201 can process physiological data obtained from physiological sensors and can execute instructions to perform functions related to storing, processing, analyzing, and/or transmitting such physiological data. In some implementations, the hardware processor 201 may be remote to other components of the physiological monitoring system 250. The hardware processor 201 may be implemented on a computing device remote to other components of the physiological monitoring system 250. The remote computing device can include a server, a phone, a computer, another wearable device, a physiological sensor, a physiological monitoring hub, or the like. The hardware processor 201 may receive and process data from the optical detector(s) 213, and/or the other sensor(s) 215 in real-time, such as when the data is collected and/or a length of time after the data is collected that is imperceptible to human senses. The hardware processor 201 may access and process data stored in the storage device 203, such as data that was previously generated by the optical detector(s) 213, and/or the other sensor(s) 215.

The storage device 203 can include one or more memory devices that store data, including without limitation, dynamic and/or static random-access memory (RAM), programmable read-only memory (PROM), erasable programmable read-only memory (EPROM), electrically erasable programmable read-only memory (EEPROM), and the like. Such stored data can include processed and/or unprocessed physiological data obtained from physiological sensors.

The communication module 205 can facilitate communication (via wired and/or wireless connection) between the physiological monitoring system 250 (and/or the components thereof) and separate devices, such as separate devices, sensors, systems, servers, or the like. For example, the communication module 205 can be configured to allow the hardware processor 201 to wirelessly communicate with other devices, systems, and/or networks over any of a variety of communication protocols. The communication module 205 can be configured to use any of a variety of wireless communication protocols, such as Wi-Fi (802.11x), Bluetooth®, ZigBee®, Z-wave®, cellular telephony, infrared, near-field communications (NFC), RFID, satellite transmission, proprietary protocols, combinations of the same, and the like. The communication module 205 can allow data and/or instructions to be transmitted and/or received to and/or from the hardware processor 201 and separate computing devices. The communication module 205 can be configured to transmit and/or receive (for example, wirelessly) processed and/or unprocessed physiological data with separate computing devices including physiological sensors, other monitoring hubs, remote servers, or the like. The communication module 205 can be embodied in one or more components that are in communication with each other. The communication module 205 can include a wireless transceiver, an antenna, and/or a near field communication (NFC) component such as a transponder.

The power source 207 can provide power for components of the physiological monitoring system 250. The power source 207 can include a battery. The power source 207 can include a dual-battery configuration with a main battery and a backup battery. The power source 207 can include energy from utility power line such as cable connecting to a 110V outlet. The power source 207 can include solar power.

The hardware processor 201 can generate display data to render a display or user interface on the display 211. The display 211 may be a digital display. The display 211 may be an LED display. The display 211 may be an ultra low power display. The display 211 may be an e-paper display. The display 211 may display physiological data such as physiological parameters.

The optical emitter(s) 209 can be configured to emit optical radiation, such as light. The optical emitter(s) 209 can include one or more light emitting diodes (LEDs). The optical emitter(s) 209 can also include one or more groups or clusters of emitters. In some implementations, each group or cluster of emitters may include five emitters. In some implementations, each group or cluster of emitters may include more than five emitters. In some implementations, each group or cluster of emitters may include four emitters. In some implementations, each group or cluster of emitters may include less than four emitters, such as three or two emitters. Each group of optical emitter(s) 209 can be configured to emit a plurality of different wavelengths such as described herein. The optical emitter(s) 209 can be configured to emit radiation at a plurality of wavelengths. The optical emitter(s) 209 can be configured to emit radiation within the visible spectrum.

The optical detector(s) 213 can include light sensitive photodetectors. The optical detector(s) 213 can include photodiodes. The optical detector(s) 213 can include more than one group or cluster of detectors. In some implementations, each group or cluster of optical detector(s) 213 may include a single detector. In some implementations, each group or cluster of optical detector(s) 213 may include more than one detector.

The optical emitter(s) 209 can be configured to emit light of a first wavelength. The first wavelength may be within a range of about 400 nm to 660 nm. The first wavelength may be within a range of about 610 nm to 630 nm. The first wavelength may be less than 700 nm. The first wavelength may be less than 650 nm. The first wavelength may be about 620 nm.

The optical emitter(s) 209 can be configured to emit light of a second wavelength. In some implementations, the second wavelength may be within a range of about 620 nm to 700 nm. The second wavelength may be within a range of about 650 nm to 670 nm. The second wavelength may be less than 700 nm. The second wavelength may be less than 680 nm. The second wavelength may be about 660 nm.

The optical emitter(s) 209 can be configured to emit light of a third wavelength. In some implementations, the third wavelength may be within a range of about 800 nm to 970 nm. The third wavelength may be within a range of about 895 nm to 915 nm. The third wavelength may be greater than 800 nm. The third wavelength may be greater than 890 nm. The third wavelength may be about 905 nm.

The optical emitter(s) 209 can be configured to emit light of a fourth wavelength. In some implementations, the fourth wavelength may be within a range of about 905 nm to 1400 nm. The fourth wavelength may be within a range of about 960 nm to 980 nm. The fourth wavelength may be greater than 900 nm. The fourth wavelength may be greater than 950 nm. The fourth wavelength may be about 970 nm.

Light of the first and/or second wavelengths may be more sensitive to tissue content of hemoglobin, such as oxy-hemoglobin and/or deoxy-hemoglobin, than light of the third and/or fourth wavelengths. Light of the first and/or second wavelengths may be more readily absorbed by hemoglobin, such as oxy-hemoglobin and/or deoxy-hemoglobin, than light of the third and/or fourth wavelengths. Light of the third and/or fourth wavelengths may be more sensitive to tissue content of water than light of the first and/or second wavelengths. Light of the third and/or fourth wavelengths may be more readily absorbed by water than light of the first and/or second wavelengths.

As an illustrative example, an implementation of the optical detector(s) 213 may include a first LED capable of emitting light at a wavelength of 620 nm, a second LED capable of emitting light at a wavelength of 660 nm, a third LED capable of emitting light at a wavelength of 905 nm, and a fourth LED capable of emitting light at a wavelength of 970 nm.

The hardware processor 201 can process signals to determine a plurality of physiological parameters. The hardware processor 201 can be configured to drive the optical emitter(s) 209 to emit radiation of different wavelengths and/or to process signals from the optical detector(s) 213 of attenuated radiation after absorption by the body tissue of the subject. The absorption of light can be via transreflectance by the wearer's body tissue. The absorption of light can be the pulsatile arterial blood flowing through the capillaries (and optionally also the arteries) within a tissue site. As used herein, "attenuation" and "absorption" may be used interchangeably.

The physiological monitoring system 250 can be configured to measure an indication of the wearer's physiological parameters. This can include, for example, pulse rate, respiration rate, SpO2, Pleth Variability Index (PVI), Perfusion Index (PI), Respiration from the pleth (RRp), total hemoglobin (SpHb), hydration, glucose, blood pressure, and/or other parameters. The physiological monitoring system 250 can perform intermittent and/or continuous monitoring of the measured parameters. The physiological monitoring system 250 can additionally and/or alternatively perform a spot check of the measured parameters, for example, upon request by the wearer.

The other sensor(s) 215 can include one or more sensors. The other sensor(s) 215 may be remote to the hardware processor 201, the optical emitter(s) 209 and/or the optical detector(s) 213. The other sensor(s) 215 can include a physiological sensor. The other sensor(s) 215 can include one or more of an acoustic sensor, a voltage sensor, an impedance sensor, a capacitive sensor, inertial sensor, or the like.

The hardware processor 201 can determine a hydration status of a subject. The hardware processor 201 can determine a hydration index of a subject. The hardware processor 201 can determine a hydration status of a subject based on data obtained from an optical sensor such as from optical emitter(s) 209 and/or optical detector(s) 213. The hardware processor 201 can determine a hydration status of a subject based on data obtained from the other sensor(s) 215. The hardware processor 201 can determine a hydration status of a subject based on a combination of data obtained from the optical emitter(s) 209, optical detector(s) 213, and the other sensor(s) 215. For example, the hardware processor 201 may determine a hydration status of a subject based on data from an optical sensor in combination with data from a sweat sensor, an impedance sensor, an inertial sensor, or an acoustic sensor. The hardware processor 201 can calculate an average or a weighted average of hydration index values calculated based on signals from the different sensors, and/or rely on the different hydration monitoring sensors for redundancy.

Figure 3:
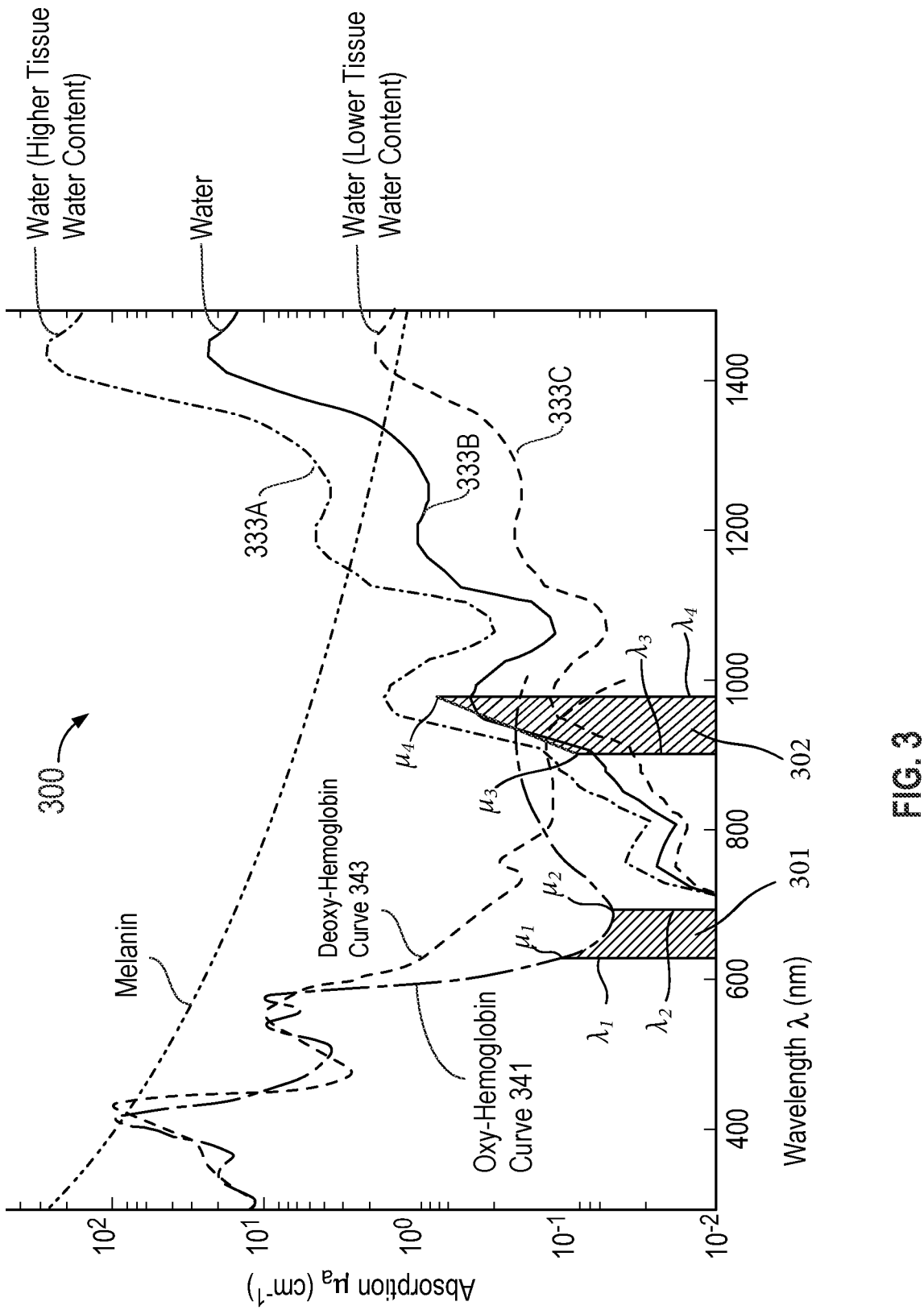
FIG. 3 is a diagram illustrating how various components of physiological tissue attenuate or absorb optical radiation at various wavelengths.

FIG. 3 is a diagram 300 illustrating how various components of physiological tissue attenuate or absorb radiation at various wavelengths. Tissue can include physiological components such as melanin, hemoglobin, water, or the like. Hemoglobin can include oxy-hemoglobin, deoxy-hemoglobin, carboxy-hemoglobin, and/or met-hemoglobin. Water can be intracellular or extracellular. Extracellular water can be interstitial or intravascular. Intravascular water can be in blood plasma. As shown, water may absorb less radiation at shorter wavelengths than at longer wavelengths. For example, water may absorb minimal or negligent amounts of radiation at wavelengths of less than about 700 nm and may absorb more radiation at wavelengths of greater than about 700 nm. The amount of radiation absorbed by water may depend on the wavelength of the radiation. The amount of radiation absorbed by water may increase as wavelength increases.

As shown, hemoglobin, such as oxy-hemoglobin, may absorb less radiation at greater wavelengths than at shorter wavelengths. For example, hemoglobin may absorb minimal or negligent amounts of radiation at wavelengths of greater than about 800 nm, 900 nm, or 1000 nm and may absorb more radiation at wavelengths of less than about 800 nm, 900 nm, or 1000 nm. The amount of radiation absorbed by hemoglobin may depend on the wavelength of the radiation. The amount of radiation absorbed by hemoglobin may increase as wavelength decreases.

Diagram 300 includes three absorption curves for various tissue water content. Curve 333A shows absorption of radiation across various wavelengths by a high tissue water content. Curve 333B shows absorption of radiation across various wavelengths by an intermediate tissue water content. Curve 333C shows absorption of radiation across various wavelengths by a low tissue water content. As shown, a change in tissue water content may affect the amount of radiation absorbed by the tissue. For example, a decrease in tissue water content may result in a decrease in absorbance of radiation in the tissue, such as for radiation of wavelengths greater than about 700 nm. As another example, an increase in tissue water content may result in an increase in absorbance of radiation in the tissue, such as for radiation of wavelengths greater than about 700 nm. As shown, a change in tissue water content may affect the amount of radiation absorbed by the tissue at wavelengths greater than about 700 nm. As shown, a change in tissue water content may have minimal, inconsequential, or no affect on the amount of radiation absorbed by the tissue at wavelengths of less than about 700 nm.

Diagram 300 includes an example first parameter 301 and an example second parameter 302. The first parameter 301 represents absorption of light integrated under the oxy-hemoglobin curve 341. The first parameter 301 may depend on hemoglobin content such as oxy-hemoglobin content. For example, the area of the first parameter 301 may increase as oxy-hemoglobin content increases and may decrease as oxy-hemoglobin content decreases. The first parameter 301 may be unaffected, substantially unaffected, or minimally affected by tissue water content. For example, changes in tissue water content may have little or no effect on the first parameter 301. The first parameter 301 may not depend on tissue water content. The first parameter 301 may be independent of tissue water content. The first parameter 301 may include wavelengths that are water-independent. The first parameter 301 may not be sensitive to water.

The second parameter 302 represents absorption of light integrated under the water absorption curve, such as curve 333B. The second parameter 302 may depend on tissue water content. For example, the area of the second parameter 302 may increase as tissue water content increase and may decrease as tissue water content decreases. The second parameter 302 may be affected by hemoglobin, such as deoxy-hemoglobin or oxy-hemoglobin content. For example, as shown, the deoxy-hemoglobin curve 343 and the oxy-hemoglobin curve 341 may intersect the second parameter 302. The second parameter 302 may correspond to the amount of water in the tissue which may correspond to a subject's hydration level. The second parameter 302 may depend more directly on tissue water content than on hemoglobin content.

As described herein, the second parameter 302 may be used to determine a subject's hydration level. In some implementations, the second parameter 302, in combination with the first parameter 301, may be used to determine a subject's hydration level. For example, the systems or methods described herein may compare the first parameter 301 to the second parameter 302. A second parameter 302 that is large relative to the first parameter 301 may indicate high tissue water content. A second parameter 302 that is small relative to the first parameter 301 may indicate low tissue water content. Accounting for how non-water components, such as hemoglobin, may affect absorption of radiation within the second parameter 302 may improve water tissue content determinations.

The first parameter 301 may be bounded by upper and lower wavelengths. The first parameter 301 may include a lower wavelength $\lambda_1$. The first parameter 301 may include an upper wavelength $\lambda_2$. The lower wavelength $\lambda_1$ may not be affected or may be minimally affected by tissue water content. The lower wavelength $\lambda_1$ may not be absorbed by water or may be minimally absorbed by water. The lower wavelength $\lambda_1$ may be referred to as a water-independent wavelength. The lower wavelength $\lambda_1$ may be less sensitive to absorption, attenuation, scattering, etc. by water than lower wavelength $\lambda_3$ and/or than upper wavelength $\lambda_4$. The lower wavelength $\lambda_1$ may not be sensitive to absorption, attenuation, scattering, etc. by water. The lower wavelength $\lambda_1$ may be less than 700 nm, less than 680 nm, less than 660 nm, less than 640 nm, less than 620 nm, less than 610 nm, less than 600 nm, less than 500 nm, etc. In some implementations, the lower wavelength $\lambda_1$ may be 620 nm. The lower wavelength $\lambda_1$ may be less than the upper wavelength $\lambda_2$. The difference between the lower wavelength $\lambda_1$ and the upper wavelength $\lambda_2$ may be less than 100 nm, less than 80 nm, less than 60 nm, less than 40 nm, less than 30 nm, etc. In some implementations, the difference between the lower wavelength $\lambda_1$ and the upper wavelength $\lambda_2$ may be 40 nm. The lower wavelength $\lambda_1$ may be located on a portion of the oxy-hemoglobin curve 341 that has a slope of absolute value that is greater than other portions of the oxy-hemoglobin curve 341. The lower wavelength $\lambda_1$ may be located on a portion of the oxy-hemoglobin curve 341 that has the greatest, or near the greatest, absolute value slope. The lower wavelength $\lambda_1$ may be separated from the upper wavelength $\lambda_2$ such that a difference between absorption of the lower wavelength $\lambda_1$ due to deoxy-hemoglobin or oxy-hemoglobin and absorption of the upper wavelength $\lambda_2$ due to deoxy-hemoglobin or oxy-hemoglobin, is at a maximum or near a maximum, for a range of wavelengths between about 400 nm and about 1000 nm or between about 500 and about 1000 nm or between about 600 nm and about 1000 nm.

The upper wavelength $\lambda_2$ may not be affected or may be minimally affected by tissue water content. The upper wavelength $\lambda_2$ may not be absorbed by water or may be minimally absorbed by water. The upper wavelength $\lambda_2$ may be referred to as a water-independent wavelength. The upper wavelength $\lambda_2$ may be less sensitive to absorption, attenuation, scattering, etc. by water than lower wavelength $\lambda_3$ and/or than upper wavelength $\lambda_4$. The upper wavelength $\lambda_2$ may not be sensitive to absorption, attenuation, scattering, etc. by water. The upper wavelength $\lambda_2$ may be less than 700 nm, less than 680 nm, less than 660 nm, less than 650 nm, less than 640 nm, etc. In some implementations, the upper wavelength $\lambda_2$ may be 660 nm. The upper wavelength $\lambda_2$ may be greater than the lower wavelength $\lambda_1$.

The second parameter 302 may be bounded by upper and lower wavelengths. The second parameter 302 may include a lower wavelength $\lambda_3$. The second parameter 302 may include an upper wavelength $\lambda_4$. The lower wavelength $\lambda_3$ may depend on tissue water content. The lower wavelength $\lambda_3$ may be absorbed by water. The lower wavelength $\lambda_3$ may be referred to as a water-dependent wavelength. The lower wavelength $\lambda_3$ may be sensitive to absorption, attenuation, scattering, etc. by water. The lower wavelength $\lambda_3$ may be more sensitive to absorption, attenuation, scattering, etc. by water than lower wavelength $\lambda_1$ and/or upper wavelength $\lambda_2$. The lower wavelength $\lambda_3$ may be referred to as water sensitive. The lower wavelength $\lambda_3$ may be greater than 700 nm. The lower wavelength $\lambda_3$ may be less than 880 nm, less than 900 nm, less than 910 nm, less than 920 nm, less than 940 nm, etc. In some implementations, the lower wavelength $\lambda_3$ may be 905 nm. The lower wavelength $\lambda_3$ may be less than the upper wavelength $\lambda_4$. The difference between the lower wavelength $\lambda_3$ and the upper wavelength $\lambda_4$ may be less than 100 nm, less than 90 nm, less than 80 nm, less than 70 nm, less than 60 nm, less than 50 nm, etc. In some implementations, the difference between the lower wavelength $\lambda_3$ and the upper wavelength $\lambda_4$ may be 65 nm. The lower wavelength $\lambda_3$ may be located on a portion of the water curve 333 that has a slope of absolute value that is greater than other portions of the water curve 333. The lower wavelength $\lambda_3$ may be located on a portion of the oxy-hemoglobin curve 341 that has the greatest, or near the greatest, absolute value slope. The lower wavelength $\lambda_3$ may be separated from the upper wavelength $\lambda_4$ such that a difference between absorption of the lower wavelength $\lambda_3$ due to water and absorption of the upper wavelength $\lambda_4$ due to water, is at a maximum or near a maximum, for a range of wavelengths between about 800 nm and about 1300 nm or between about 800 nm and about 1000 nm.

The upper wavelength $\lambda_4$ may depend on tissue water content. The upper wavelength $\lambda_4$ may by absorbed by water. The upper wavelength $\lambda_4$ may be referred to as a water-dependent wavelength. The upper wavelength $\lambda_4$ may be sensitive to absorption, attenuation, scattering, etc. by water. The upper wavelength $\lambda_4$ may be more sensitive to absorption, attenuation, scattering, etc. by water than lower wavelength $\lambda_1$ and/or upper wavelength $\lambda_2$. The upper wavelength $\lambda_4$ may be referred to as water sensitive. The upper wavelength $\lambda_4$ may be greater than 700 nm. The upper wavelength $\lambda_4$ may be less than 950 nm, less than 960 nm, less than 970 nm, less than 980 nm, less than 990 nm, less than 1000 nm, etc. In some implementations, the upper wavelength $\lambda_4$ may be 970 nm. The upper wavelength $\lambda_4$ may be greater than the lower wavelength $\lambda_3$.

As shown with respect to the first parameter 301, the lower wavelength $\lambda_1$ may correspond to an absorption parameter $\mu_1$, and the upper wavelength $\lambda_2$ may correspond to an absorption parameter $\mu_2$. As shown with respect to the second parameter 302, the lower wavelength $\lambda_3$ may correspond to an absorption parameter $\mu_3$, and the upper wavelength $\lambda_4$ may correspond to an absorption parameter $\mu_4$. The absorption parameters may indicate an amount radiation absorbed at that wavelength by a medium as the radiation travels through the medium. For example, the absorption parameter $\mu_1$ may indicate the amount of light having a wavelength of $\lambda_1$ that is absorbed by the tissue. The absorption parameters may correspond to an intensity of radiation detected at a detector such as a light sensor, at photodiode, or the like. For example, a high absorption parameter may correspond to a small light intensity detected at a detector which may indicate that much of the light at that wavelength was absorbed as it travelled through the medium. As another example, a small absorption parameter may correspond to a large light intensity detected at a detector which may indicate that a small amount of the light at that wavelength was absorbed as it travelled through the medium. The absorption parameter and/or intensity of radiation detected may correspond to a brightness of light detected. The absorption parameter $\mu_1$ may be greater than the absorption parameter $\mu_2$. The absorption parameter $\mu_4$ may be greater than the absorption parameter $\mu_3$.

The absorption parameter $\mu_1$ may correspond to absorption of radiation by hemoglobin such as oxy-hemoglobin. Hemoglobin such as oxy-hemoglobin absorption may account for a majority of the absorption parameter $\mu_1$. Water may not affect, or may have minimal affect on, the absorption parameter $\mu_1$. The absorption parameter $\mu_2$ may correspond to absorption of radiation by hemoglobin such as oxy-hemoglobin. Hemoglobin such as oxy-hemoglobin absorption may account for a majority of the absorption parameter $\mu_2$. Water may not affect, or may have minimal affect on, the absorption parameter $\mu_2$. The absorption parameter $\mu_3$ may correspond to absorption of radiation by water. The absorption parameter $\mu_3$ may correspond to absorption of radiation by non-water tissue components such as hemoglobin. A majority of absorption parameter $\mu_3$ may correspond to absorption of radiation by water. As shown, the absorption parameter $\mu_3$ may not exactly correspond to the water curve 333. For example, the absorption parameter $\mu_3$ may be greater than the water curve 333, at least because both water and non-water tissue components, such as deoxy-hemoglobin or oxy-hemoglobin, absorb radiation at the lower wavelength $\lambda_3$. The absorption parameter $\mu_4$ may correspond to absorption of radiation by water. The absorption parameter $\mu_4$ may correspond to absorption of radiation by non-water tissue components such as deoxy-hemoglobin or oxy-hemoglobin. A majority of absorption parameter $\mu_4$ may correspond to absorption of radiation by water. As shown, the absorption parameter $\mu_4$ may not exactly correspond to the water curve 333. For example, the absorption parameter $\mu_4$ may be greater than the water curve 333, at least because both water and non-water tissue components, such as deoxy-hemoglobin or oxy-hemoglobin, absorb radiation at the upper wavelength $\lambda_4$.

The absorption parameter $\mu_3$ may provide an indication of the amount of water in a subject's tissue. The absorption parameter $\mu_4$ may provide an indication of the amount of water in a subject's tissue. A hydration estimation based solely on absorption parameter $\mu_3$ and/or absorption parameter $\mu_4$ may not correspond exactly to the subject's hydration at least because absorption parameter $\mu_3$ and/or absorption parameter $\mu_4$ may be affected by non-water tissue components. Systems or methods, such as described herein, may improve a hydration estimation by accounting for absorption due to non-water components, such as by considering absorption parameter $\mu_1$ and/or absorption parameter $\mu_2$, such as in combination with absorption parameter $\mu_3$ and/or absorption parameter $\mu_4$. Variations in a subject's hemoglobin levels, such as $SpO_2$ levels, may have little to no influence on a hydration estimate. In some implementations, if a subject's $SpO_2$ is less than 95%, the second parameter 302 may be normalized by projecting the absorbance of its lower bound and the upper bound absorbances to their respective values if the subject's $SpO_2$ was 95% or greater.

A hardware processor may estimate a subject's hydration level which may also be referred to herein as a hydration index. The hydration index may be based on the amount of water within a tissue of the subject. The hardware processor may determine an amount of water in the subject's tissue. The processor may be any of the example processors shown and/or described herein, such as hardware processor 201. The processor may be implemented in a wearable device. The processor may be remote to a wearable device.

The hardware processor may estimate a hydration index based on the second parameter 302, alone or in combination with, the first parameter 301. The second parameter 302 may include an area of the second parameter 302, lower wavelength $\lambda_3$, upper wavelength $\lambda_4$, absorption parameter $\mu_3$ (which may correspond to a light intensity detected at a detector), and/or absorption parameter $\mu_4$ (which may correspond to a light intensity detected at a detector). The first parameter 301 may include an area of the first parameter 301, lower wavelength $\lambda_1$, upper wavelength $\lambda_2$, absorption parameter $\mu_1$ (which may correspond to a light intensity detected at a detector), and/or absorption parameter $\mu_2$ (which may correspond to a light intensity detected at a detector).

The hardware processor may account for absorption due to non-water tissue components within second parameter 302, such as by normalizing the second parameter 302 with the first parameter 301. The hardware processor may account for absorption due to non-water tissue components within second parameter 302, such as by subtracting first parameter 301, or portions thereof, from the second parameter 302, or portions thereof. The hardware processor may account for variations in sensitivity of a detector. The sensitivity of a detector, such as a photodiode, may vary according to wavelength of radiation detected. For example, a detector may be less sensitive to detecting radiation at wavelengths at or around $\mu_4$ and may be more sensitive to detecting wavelengths at or around $\mu_3$. The hardware processor can adjust the output received from the detector based on wavelength to compensate for wavelength-based detector sensitivities. For example, the hardware processor may amplify a magnitude of a detector signal corresponding to a wavelength at which the detector is less sensitive to account for the detector's reduced ability to detect those wavelengths. As another example, the hardware processor may decrease or not change a magnitude of a detector signal corresponding to a wavelength at which the detector has a heightened or average sensitivity. In one example implementation, the hardware processor may amplify detector signals corresponding to wavelengths at or around $\mu_4$ and may decrease or not change detector signals corresponding to wavelengths at or around $\mu_3$. Testing during manufacturing can be used to determine when compensation maybe needed and to what level. Compensation levels can be saved into memory incorporated into each individual device or sensor.

The hardware processor can estimate an area of first parameter 301. The area of first parameter 301 may correspond approximately to the area bounded by lower wavelength $\lambda_1$, upper wavelength $\lambda_2$, and the oxy-hemoglobin curve 341. The hardware processor can estimate an area of second parameter 302. The area of second parameter 302 may correspond approximately to the area bounded by lower wavelength $\lambda_3$, upper wavelength $\lambda_4$, and the water curve 333. In some implementations, the hardware processor may determine the area of first parameter 301, according to equation (3), as follows:

$$\text{area of first parameter } 301 = \left(\frac{\mu_2 + \mu_1}{2}\right)(\lambda_2 - \lambda_1). \tag{3}$$

In some implementations, the hardware processor may determine the area of second parameter 302, according to equation (4), as follows:

$$\text{area of second parameter } 302 = \left(\frac{\mu_4 + \mu_3}{2}\right)(\lambda_4 - \lambda_3). \tag{4}$$

The hardware processor can estimate a portion of an area of first parameter 301. The area of the portion of the first parameter 301 may be less than the area bounded by lower wavelength $\lambda_1$, upper wavelength $\lambda_2$, and the oxy-hemoglobin curve 341. The hardware processor can estimate a portion of an area of second parameter 302. The area of the portion of the second parameter 302 may be less than the area bounded by lower wavelength $\lambda_3$, upper wavelength $\lambda_4$, and the water curve 333. In some implementations, the hardware processor may determine a portion of the area of first parameter 301, according to equation (5), as follows:

$$\text{area of first parameter } 301 = \left(\frac{(\mu_1 - \mu_2)(\lambda_2 - \lambda_1)}{2}\right). \tag{5}$$

In some implementations, the hardware processor may determine a portion of the area of second parameter 302, according to equation (6), as follows:

$$\text{area of first parameter } 302 = \left(\frac{(\mu_4 - \mu_3)(\lambda_4 - \lambda_3)}{2}\right). \tag{6}$$

The hardware processor can determine an area of first parameter 301. The hardware processor may determine the area of the first parameter 301 by integrating the oxy-hemoglobin curve 341 between the lower wavelength $\lambda_1$ and the upper wavelength $\lambda_2$. In some implementations, the processor may determine absorption of radiation at additional wavelengths within first parameter 301, such as at wavelengths between lower wavelength $\lambda_1$ and upper wavelength $\lambda_2$. Measuring absorption of one or more additional wavelengths may improve an accuracy of estimating the area under an absorption curve. In some implementations, the hardware processor may integrate the area under the oxy-hemoglobin curve 341 based on at least the absorption of one or more additional wavelengths between lower wavelength $\lambda_1$ and upper wavelength $\lambda_2$.

The hardware processor can determine an area of second parameter 302. The hardware processor may determine the area of the second parameter 302 by integrating the oxy-hemoglobin curve 341 between the lower wavelength $\lambda_3$ and the upper wavelength $\lambda_4$. In some implementations, the processor may determine absorption of radiation at additional wavelengths within second parameter 302, such as at wavelengths between lower wavelength $\lambda_3$ and upper wavelength $\lambda_4$. Measuring absorption of one or more additional wavelengths may improve an accuracy of estimating the area under an absorption curve. In some implementations, the hardware processor may integrate the area under the water curve 333 based on at least the absorption of one or more additional wavelengths between lower wavelength $\lambda_3$ and upper wavelength $\lambda_4$.

The hardware processor can determine a hydration index of a subject based on an area, or a portion of an area, of second parameter 302, alone or in combination with, an area, or a portion of an area, of first parameter 301. The hardware processor can determine a hydration index by subtracting an area of first parameter 301, or portion thereof, from an area of second parameter 302, or portion thereof. As an example, the hardware processor may calculate a hydration index of a subject by subtracting an area of first parameter 301 calculated according to equation (3) from an area of second parameter 302 calculated according to equation (4). As another example, the hardware processor may calculate a hydration index of a subject by subtracting a portion of an area of first parameter 301 calculated according to equation (5) from a portion of an area of second parameter 302 calculated according to equation (6).

The hardware processor can determine a hydration index by normalizing an area of second parameter 302, or portion thereof, with an area of first parameter 301, or portion thereof. As an example, the hardware processor may calculate a hydration index of a subject by dividing an area of second parameter 302 calculated according to equation (4) by an area of first parameter 301 calculated according to equation (3). As another example, the hardware processor may calculate a hydration index of a subject by dividing a portion of an area of second parameter 302 calculated according to equation (6) by a portion of an area of first parameter 301 calculated according to equation (5).

The hardware processor can determine a hydration index based on the intensity of light measured through a medium such as tissue of a subject. The hardware processor can determine a hydration index based on the intensity of light at a plurality of wavelengths measured through the tissue of a subject. The hardware processor can determine a hydration index based on a ratio of intensity of light measured through the tissue of a subject to an intensity of light measured through a reference material. The reference material can be air. The hardware processor can determine a hydration index based on a difference in ratios of intensities of light.

The difference in intensity of light observed through two materials may be proportional to the difference in their respective optical densities. The hardware processor may determine a change, or difference, in optical densities between two materials according to equation (7), as follows:

$$\Delta\text{optical density} = \ln\left(\frac{I_\beta}{I_\alpha}\right). \tag{7}$$

As discussed herein, I parameters, such as $I_\beta$ or $I_\alpha$ may correlate to intensity of light measured through a medium. I parameters may correlate to attenuation or absorption of radiation by a medium through which it travels. I parameters may be inversely related to attenuation or absorption of radiation. I parameters may correlate to brightness of light detected at a detector. I parameters may be directly related to brightness of light detected at a detector. I parameters may correspond to a parameter generated by a detector, such as a DC value. I parameters may be normalized by current. Accordingly, I parameters may be independent of current. I parameters may be normalized by gain. Accordingly, I parameters may be independent of gain. I parameters may be independent of emitter operation, such as if one LED emits light more brightly than other LEDs the I parameters may be normalized to account for such differences.

$I_\beta$ may be the measured intensity of light through a medium such as tissue of a subject. The hardware processor may determine $I_\beta$ at a plurality of different times, such as whenever performing a measurement to determine a subject's hydration. $I_\beta$ may change as the hydration level of a subject changes. In some implementations, the processor may adjust $I_\beta$ based on known or determined wavelength-based detector sensitivities. For example, the processor may increase or amplify $I_\beta$ if the corresponding wavelength falls within certain thresholds. As another example, the processor may reduce or decrease $I_\beta$ if the corresponding wavelength falls within certain thresholds. As another example, the processor may not change $I_\beta$ if the corresponding wavelength falls within certain thresholds.

$I_\alpha$ may be the measured intensity of light through a reference material. The reference material may be air. In some implementations, the hardware processor may use the same $I_\alpha$ value whenever performing a measurement to determine a subject's hydration. The value of $I_\alpha$ may not change. The hardware processor may determine $I_\alpha$ by accessing data, such as data stored in memory. In some implementations, $I_\alpha$ may be the average light intensity measured through a reference material using a plurality of sensors. In some implementations, $I_\alpha$ may be the light intensity measured through a reference material using a specific sensor, such as the same sensor used to determine $I_\beta$. For example, a wearable device may perform a calibration to determine values of $I_\alpha$ that correspond to each of the sensors on that specific wearable device. A wearable device may perform a single calibration to determine values of $I_\alpha$ such as during manufacturing. A wearable device may perform a plurality of calibrations to determine, or update, the values of $I_\alpha$, such as on a periodic basis, or on demand. In some implementations, a measured intensity may be based on a current divided by a gain.

The hardware processor can determine a hydration index based on normalizing a water-dependent optical parameter with a water-independent optical parameter. The optical parameters may be based on an optical intensity of detected wavelengths. The optical parameters may be based on absorption of detected wavelengths in a medium. In some implementations, the hardware processor may determine a hydration index of a subject according to equation (8.1), as follows:

$$\text{hydration index} = C \times \frac{\ln\left(I_{\beta(\lambda_{3,4})}\right)}{\ln\left(I_{\beta(\lambda_{1,2})}\right)}.$$ (8.1)

The water-dependent optical parameter $\ln(I_{\beta(\lambda_{3,4})})$ may be based on wavelength $\lambda_3$ or wavelength $\lambda_4$, or any wavelength therebetween, which may correspond to wavelengths $\lambda_3$ or $\lambda_4$ described with reference to FIG. 3. The water-independent optical parameter $\ln(I_{\beta(\lambda_{1,2})})$ may be based on wavelength $\lambda_1$ or wavelength $\lambda_2$, or any wavelength therebetween, which may correspond to wavelengths $\lambda_1$ or $\lambda_2$ described with reference to FIG. 3. C may be a constant such as described in greater detail further below.

The hardware processor can determine a hydration index based on normalizing a normalized water-dependent optical parameter to a normalized water-independent optical parameter. The normalized optical parameters may be based on an optical intensity of detected wavelengths. The normalized optical parameters may be based on absorption of detected wavelengths in a medium. In some implementations, the hardware processor may determine a hydration index of a subject according to equation (8.2), as follows:

$$\text{hydration index} = C \times \frac{\ln\left(\frac{I_{\beta(\lambda_{3,4})}}{I_{\alpha(\lambda_{3,4})}}\right)}{\ln\left(\frac{I_{\beta(\lambda_{1,2})}}{I_{\alpha(\lambda_{1,2})}}\right)}.$$ (8.2)

The processor may normalize the optical parameters by normalizing a measurement of radiation through a tissue material with a measurement of radiation through a reference material. The normalized water-dependent optical parameter $$\ln\left(\frac{I_{\beta(\lambda_{3,4})}}{I_{\alpha(\lambda_{3,4})}}\right)$$

may be based on wavelength $\lambda_3$ or wavelength $\lambda_4$, or any wavelength therebetween, which may correspond to wavelengths $\lambda_3$ or $\lambda_4$ described with reference to FIG. 3. The normalized water-independent optical parameter $$\ln\left(\frac{I_{\beta(\lambda_{1,2})}}{I_{\alpha(\lambda_{1,2})}}\right)$$

may be based on wavelength $\lambda_1$ or wavelength $\lambda_2$, or any wavelength therebetween, which may correspond to wavelengths $\lambda_1$ or $\lambda_2$ described with reference to FIG. 3. C may be a constant such as described in greater detail further below.

The hardware processor can determine a hydration index based on normalizing a difference in water-dependent optical parameters to a difference in water-independent optical parameters. The optical parameters may be based on an optical intensity of detected wavelengths. The optical parameters may be based on absorption of detected wavelengths in a medium. In some implementations, the hardware processor may determine a hydration index of a subject according to equation (8.3), as follows:

$$\text{hydration index} = C \times \frac{\ln\left(I_{\beta(\lambda_4)}\right) - \ln\left(I_{\beta(\lambda_3)}\right)}{\ln\left(I_{\beta(\lambda_1)}\right) - \ln\left(I_{\beta(\lambda_2)}\right)}.$$ (8.3)

The water-dependent optical parameter $\ln(I_{\beta(\lambda_3)})$ may be based on wavelength $\lambda_3$ which may correspond to wavelength $\lambda_3$ described with reference to FIG. 3. The water-dependent optical parameter $\ln(I_{\beta(\lambda_4)})$ may be based on wavelength 24, which may correspond to wavelength $\lambda_4$ described with reference to FIG. 3. The water-independent optical parameter $\ln(I_{\beta(\lambda_1)})$ may be based on wavelength $\lambda_1$ which may correspond to wavelength $\lambda_1$ described with reference to FIG. 3. The water-independent optical parameter $\ln(I_{\beta(\lambda_2)})$ may be based on wavelength $\lambda_2$, which may correspond to wavelength $\lambda_2$ described with reference to FIG. 3. C may be a constant such as described in greater detail further below.

The hardware processor can determine a hydration index based on normalizing a difference in normalized water-dependent optical parameters to a difference in normalized water-independent optical parameters. The optical parameters may be based on an optical intensity of detected wavelengths. The optical parameters may be based on absorption of detected wavelengths in a medium. The hardware processor can determine a hydration index based on a difference in changes of optical densities of water-sensitive radiation wavelengths normalized to a difference in changes of optical densities of water-insensitive radiation wavelengths. The hardware processor can determine a hydration index based on a change in the difference of optical densities of infrared radiation wavelengths normalized to differences in changes of optical densities of red radiation wavelengths.

In some implementations, the hardware processor may determine a hydration index of a subject according to equation (8.4), as follows:

$$\text{hydration index} = C \times \frac{\ln\left(\frac{(I_{\beta(\lambda_4)})}{(I_{\alpha(\lambda_4)})}\right) - \ln\left(\frac{(I_{\beta(\lambda_3)})}{(I_{\alpha(\lambda_3)})}\right)}{\ln\left(\frac{(I_{\beta(\lambda_1)})}{(I_{\alpha(\lambda_1)})}\right) - \ln\left(\frac{(I_{\beta(\lambda_2)})}{(I_{\alpha(\lambda_2)})}\right)}. \quad (8.4)$$

The water-dependent optical parameter $$\ln\left(\frac{I_{\beta(\lambda_3)}}{I_{\alpha(\lambda_3)}}\right)$$

may be based on wavelength $\lambda_3$ which may correspond to wavelength $\lambda_3$ described with reference to FIG. 3. The water-dependent optical parameter $$\ln\left(\frac{I_{\beta(\lambda_4)}}{I_{\alpha(\lambda_4)}}\right)$$

may be based on wavelength $\lambda_4$, which may correspond to wavelength $\lambda_4$ described with reference to FIG. 3. The water-independent optical parameter $$\ln\left(\frac{I_{\beta(\lambda_1)}}{I_{\alpha(\lambda_1)}}\right)$$

may be based on wavelength $\lambda_1$ which may correspond to wavelength $\lambda_1$ described with reference to FIG. 3. The water-independent optical parameter $$\ln\left(\frac{I_{\beta(\lambda_2)}}{I_{\alpha(\lambda_2)}}\right)$$

may be based on wavelength $\lambda_2$, which may correspond to wavelength $\lambda_2$ described with reference to FIG. 3. C may be a constant such as described in greater detail further below.

For any of equations (8.1)-(8.4), the hydration index (Hi) may be a percent of total body water. The hydration index may be an amount of water. For any of equations (8.1)-(8.4), C may be a certain value for male subjects and a different value for female subjects. C may be based on the subject and may change from subject to subject or may change with time for a single subject. C may represent the total body water of a subject. C may be based on age, height, and/or weight of a subject. In some implementations, the hardware processor may determine a C value according to equation (9) or equation (10), as follows:

$$C = 2.447 - (0.09516*age) + (0.1074*height) + (0.3362*weight) \quad (9).$$

$$C = -2.097 + (0.1069*height) + (0.2466*weight) \quad (10).$$

Equation 9 may correspond to a C value for males. Equation 10 may correspond to a C value for females. Age may be measured in years. Height may be measured in centimeters. Weight may be measured in kilograms.

In some implementations, the absorption parameters in any of equations (3)-(6) may correspond to optical parameters described in any of equations (8.1)-(8.4), and vice versa.

Figure 4:
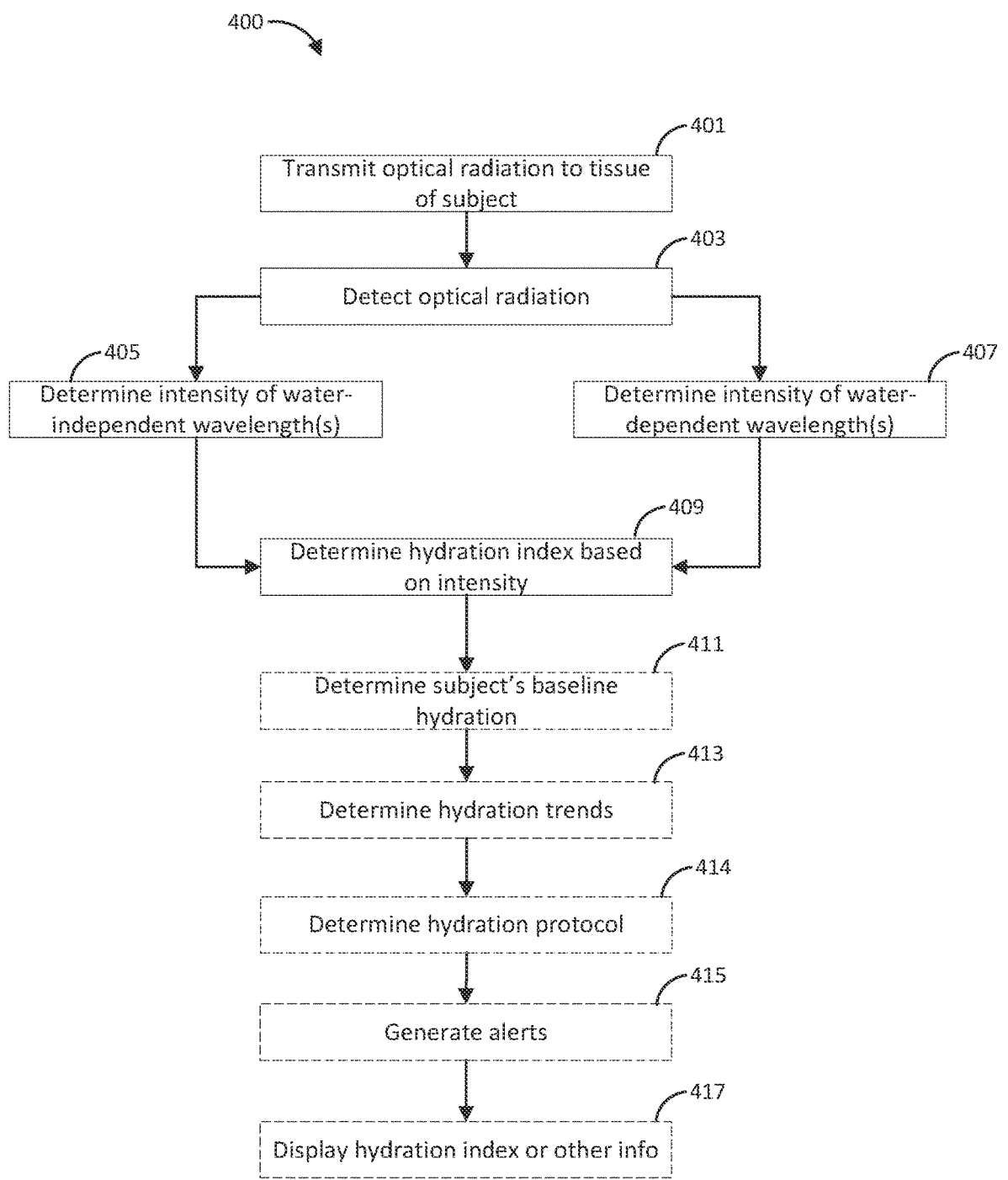
FIG. 4 is a flowchart illustrating an example process for determining a subject's hydration using optical sensors.

FIG. 4 is a flowchart illustrating an example process 400 for determining a subject's hydration using optical sensors. Process 400, or portions thereof, can be implemented on one or more devices, such as a wearable device, a computing device, a physiological sensor, a server, or the like. One or more hardware processors may execute program instructions to perform process 400, or portions thereof. In some implementations, physiological monitoring system 250, shown and/or described herein, may perform process 400, or portions thereof. In some implementations, hardware processor 201, shown and/or described herein, may perform process 400, or portions thereof. Process 400 is provided as an example and is not intended to be limiting of the present disclosure. In some implementations, the computing device(s) or hardware processor(s) performing process 400 may omit portions of the process 400, may add additional operations, and/or may rearrange an order in which the operations of the process 400 are executed.

The processor can perform process 400, or portions thereof, for individual points of data. The processor can perform process 400, or portions thereof, for a plurality of data points. The processor can perform process 400, or portions thereof, for a window of data. The window of data can include data within a period of time such as a window of 1 minute, 5 minutes, 10 minutes, 15 minutes, 20 minutes, 30 minutes, 60 minutes, etc. As an example, the processor may determine a hydration index at block 409 based on a 15-minute window of data. The processor can update the window of data by taking new measurements of data. The processor can update the window of data on a periodic basis such as every half second, every second, every 2 seconds, every 5 seconds, every 10 seconds, every 60 seconds, etc. As an example, the processor may cause sensor(s) to take a new measurement every second.

At block 401, the processor can cause an optical radiation emitter to transmit optical radiation to a medium such as a tissue of a subject. The optical radiation can include light. The optical radiation can include radiation of a plurality of wavelengths. The tissue of a subject may include skin of the subject. The tissue of the subject may be a finger, a wrist, an ear, a nose, an ankle, a toe, a foot, a leg, an arm, a head, a neck, by way of non-limiting examples. In some implementations, one or more LEDs may emit the optical radiation. In some implementations, the processor may cause the optical emitter to emit radiation on a periodic basis. In some implementations, the processor may cause the optical emitter to emit radiation in response to a condition, such as in response to a user request.

At block 403, one or more optical detectors may detect radiation. The radiation can include optical radiation emitted from the emitters at block 401. The optical detectors can include light detectors, photodiodes, or the like. Radiation detected by the detectors at block 403 may have travelled through tissue of a subject. Less than all of the radiation emitted by emitters may be detected by the detectors at block 403 at least because a portion of the radiation may have been attenuated or absorbed by the tissue of the subject.

At block 405, the processor can determine an intensity of detected water-independent radiation wavelengths. Water-independent wavelengths can include wavelengths of radiation that are minimally absorbed by water. Water-independent wavelengths can include one or more wavelengths. In some implementations, water-independent wavelengths can include two wavelengths. Water-independent wavelengths can include radiation at less than 700 nm, less than 680 nm, less than 660 nm, less than 640 nm, less than 620 nm, less than 600 nm, etc. Water-independent wavelengths can include radiation at 620 nm. Water-independent wavelengths can include radiation at 660 nm.

At block 407, the processor can determine an intensity of detected water-dependent radiation wavelengths. Water-dependent wavelengths can include wavelengths of radiation that are absorbed by water. Water-dependent wavelengths can include one or more wavelengths. In some implementations, water-dependent wavelengths can include two wavelengths. Water-dependent wavelengths can include radiation at greater than 700 nm. Water-dependent wavelengths can include radiation at less than 1400 nm, less than 1200 nm, less than 1000 nm, etc. Water-dependent wavelengths can include radiation at less than 990 nm, less than 970 nm, less than 950 nm, less than 930 nm, less than 910 nm, less than 900 nm, etc. Water-dependent wavelengths can include radiation at 970 nm. Water-dependent wavelengths can include radiation at 905 nm.

Intensity of detected wavelengths may correspond to absorption of those wavelengths by the medium. For example, a high intensity of radiation detected of a particular wavelength may correspond to a low absorption of radiation at that wavelength. As another example, a low intensity of radiation detected of a particular wavelength may correspond to a high absorption of radiation at that wavelength. Determining intensity can include determining absorption, and vice versa.

At block 409, the processor can determine a hydration index. The processor can determine the hydration index based on detected radiation intensities determined at block 405 and/or block 407. The processor can determine the hydration index based on absorptions determined at block 405 and/or block 407. The hydration index may indicate an amount or percentage of water in the subject's body. The processor can determine the hydration index according to any of the example equations described herein. The processor can determine the hydration index based on equation (3) and/or equation (4). For example, the processor may subtract an area of a water-independent parameter from an area of a water-dependent parameter. As another example, the processor can normalize the area of a water-dependent parameter by the area of a water-independent parameter. The processor can determine the hydration index based on equation (5) and/or equation (6). For example, the processor may subtract a portion of an area of a water-independent parameter from a portion of an area of a water-dependent parameter. As another example, the processor can normalize a portion of an area of a water-dependent parameter by a portion of an area of a water-independent parameter. The processor can determine the hydration index based on equation (7) and/or any of equations (8.1)-(8.4). For example, the hardware processor can determine a hydration index based on a difference in normalized detected intensities.

The processor can perform block 409 for an individual measurement of data. The processor can perform block 409 for a plurality of data measurements. The processor can perform block 409 for a plurality of data measurements within a window of time such as a 15-window. The hydration index may be based on a plurality of measurements. The hydration index may be based on a trend, average, and/or weighted average of a plurality of measurements.

At block 411, the processor can optionally determine the subject's baseline hydration. A baseline hydration may also be referred to as a reference hydration. The processor may determine the baseline hydration based on accessing information from memory, such as a previously determined baseline hydration. The processor may determine the baseline hydration based on a single measurement. For example, the processor can determine a baseline hydration based on a measurement taken the first time the subject uses a system for optical hydration measurement. As an illustrative example, the system may make a measurement and generate a baseline within the first 24-hour period that the subject uses the system. As another example, the processor can determine a baseline hydration based on a measurement taken at a particular time. As an illustrative example, the processor can determine a subject's baseline hydration based on a measurement taken at 12 AM, 1 AM, 2 AM, 3 AM, 4 AM, 5 AM, 6 AM, 8 AM, 9 AM, 10 AM, 11 AM, 12 PM, 1 PM, 2 PM, 3 PM, 4 PM, 5 PM, 6 PM, 7 PM, 8 PM, 9 PM, 10 PM, 11 PM, or other times in between these times may be suitable times for a measurement used in calculating a user's baseline hydration. In some implementations, the processor can determine a baseline hydration based on when hydration measurements are substantially constant. In some implementations, the processor can determine a baseline hydration based on information from other sensors. For example, the processor may determine a baseline hydration when information from a motion sensor, such as an inertial sensor, accelerometer, and/or gyroscope indicates that motion is substantially constant or minimal or zero acceleration.

In some implementations, the processor can determine a baseline hydration once. In some implementations, the processor can determine, or update, the baseline hydration periodically, such as once per day, etc.

In some implementations, the processor can determine a baseline hydration for a subject based on a plurality of measurements. The plurality of measurements may be at set intervals within a period of time. The period of time may be within minutes, within hours, within days, or within weeks. As an illustrative example, the processor may use an hourly series of measurements over the span of a day to generate a baseline hydration. As another illustrative example, the processor may use a series of measurements taken multi-hourly over a week to generate a baseline hydration. Other measurement frequencies and periods may also be suitable.

The processor can determine the subject's baseline hydration based on averaging a plurality of measurements. In some implementations, the average may be a weighted average. In some implementations, the weights of the weighted average may be based on a confidence score associated with the measurements. In some implementations, the weights of the weighted average may be based on factors associated with the measurements, such as time of the measurement, activity level of the subject during the measurement, information from other sensors, such as motion data from an inertial sensor, rate of change of hydration during the measurements, etc. The processor can determine the subject's baseline hydration based on a mean of a plurality of measurements. The processor can determine the subject's baseline hydration based on a median of a plurality of measurements. The processor can determine the subject's baseline hydration based on a standard deviation of a plurality of measurements. The processor can determine the subject's baseline hydration based on a trend of a plurality of measurements. The processor can determine the subject's baseline hydration based on a plurality of previously determined hydration baselines, such as an average, median, or mean of historic hydration baselines.

In some implementations, the processor can determine a baseline hydration for a subject in response to a user request. For example, a user may request to determine baseline hydration prior to commencing physical activity. In some implementations, the processor can determine a baseline hydration for a subject in response to one or more conditions.

In some implementations, the processor can determine a baseline hydration based on a dataset of hydration information. The dataset may be publicly available. The processor may access the dataset. The dataset may be stored in memory. The dataset may include hydration data from a plurality of subjects. The dataset may include hydration data from only a single subject such as the user.

The processor can update the hydration index based on the hydration baseline. The processor may determine or update the hydration index as a function of the baseline hydration. The processor can determine or update the hydration index by normalizing the hydration index to the baseline hydration. The processor may determine the hydration index as a percentage of the baseline hydration. As an example, if the processor determines that the value of the hydration index determined at block 409 is 94% of the baseline hydration, then the processor may determine that the hydration index is 0.94 or 94%, or 94.

At block 413, the processor can optionally determine trends of the hydration index or hydration status of the subject. The processor can access historic hydration indices based on previous measurements. The processor can compare historic hydration indices with a current, or most recent, hydration index. The processor can determine a trend of hydration indices. The processor can predict future hydration indices. The processor may predict future hydration indices based on a trend of historic hydration indices. The processor may monitor trends of the hydration indices.

At block 414, the processor can determine a hydration protocol. The hydration protocol may be based on one or more of the hydration index, the baseline hydration, and/or the hydration trends. The hydration protocol may be based on information from other sensors such as motion data from inertial sensors. The hydration protocol may be based on user input such as an indication of when or how the subject will exercise. The hydration protocol may include one or more recommendations to a subject. The hydration protocol may indicate an amount of water or fluids for a subject to consume. The hydration protocol may indicate a time for a subject to consume fluids. The hydration protocol may facilitate the subject maintaining or obtaining optimal hydration levels such as for a specific activity, like exercising. The hydration protocol may indicate an estimated time until a hydration index exceeds a threshold, such as rises above a threshold or drops below a threshold. The hydration protocol may indicate an estimated time until the subject is dehydrated. The hydration protocol may indicate an estimated time until the subject is re-hydrated or properly hydrated.

At block 415, the processor can optionally generate one or more alerts. The processor may generate the alerts based on one or more of the hydration index, the baseline hydration, the hydration trends, and/or the hydration protocol. In some implementations, the alerts may be based on other information, such as time of day, activity of the subject, etc. The alerts can indicate information to a subject relating to a hydration status of the subject. The alert may indicate that the subject's hydration index is below a threshold. The alert may indicate that the subject's hydration index is below the baseline hydration. The alert may indicate that a plurality of hydration indices are below a threshold, such as below the baseline hydration. The alert may indicate that a predicted future hydration status of the subject will be below a threshold, such as below a baseline hydration. The alert may indicate a hydration protocol. The alert may indicate a suggested amount of water for the subject to consume. The alert may indicate a suggested time for the subject to consume water. The alert may indicate that a hydration measurement is being taken. The alert may indicate that a hydration baseline measurement is being taken. The alert may indicate a predicted amount of time until the subject's hydration index exceeds a threshold, such as falls below a baseline hydration. The alert may indicate a predicted amount of water the subject would need to consume to change the hydration index by a certain amount.

At block 417, the processor can optionally generate display data to render a display on a display interface. The display can include one or more of the hydration index, historic hydration indices, a baseline hydration, hydration trends, and/or alerts. The display interface can include a display on a wearable device. The display interface can be a display that is remote to an optical sensor used to perform a hydration measurement. The display interface can be display 211 shown and/or described herein.

Figure 5:
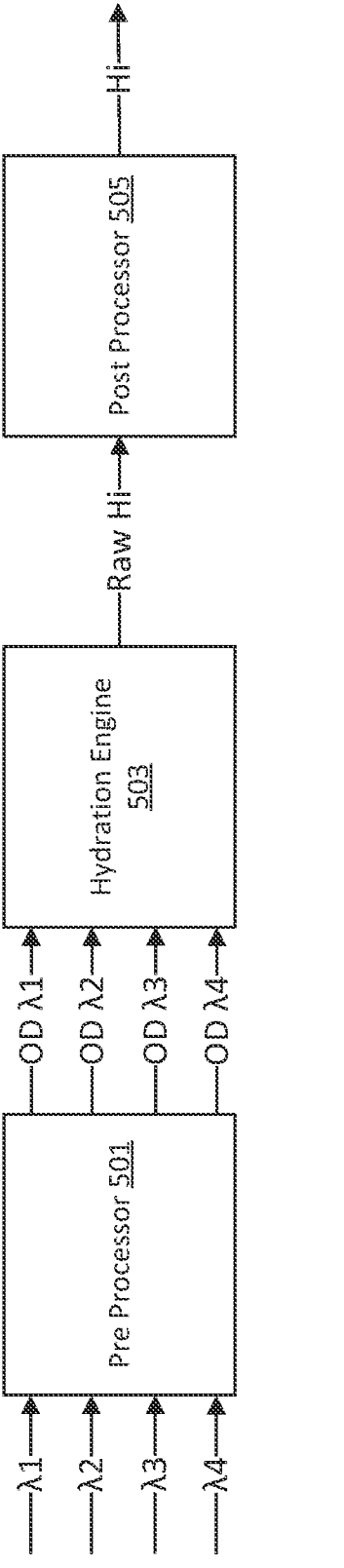
FIG. 5 is a block diagram illustrating an example implementation of determining hydration.

FIG. 5 is a block diagram illustrating an example implementation of determining hydration. One or more hardware processors, such as hardware processor 201, or any of the other example processors described herein, may implement the operations and/or processes shown and/or described in FIG. 5. A preprocessor 501 can receive one or more signals corresponding to one or more wavelengths of radiation. The preprocessor 501 may receive the signals from a detector in response to the detector detecting radiation that has travelled through a medium such as tissue of a subject. The wavelengths $\lambda_1, \lambda_2, \lambda_3, \lambda_4$, may correspond to wavelengths $\lambda_1, \lambda_2, \lambda_3, \lambda_4$, shown and/or described with reference to FIG. 3. The wavelengths $\lambda_1, \lambda_2, \lambda_3, \lambda_4$, can include any of the example wavelengths discussed with reference to FIG. 3. In some implementations, the preprocessor 501 may receive information relating to more than four wavelengths or fewer than four wavelengths. The preprocessor 501 may filter the data received. The preprocessor 501 may discard some of the data received. The preprocessor 501 may decimate the data received. The preprocessor 501 may normalize the data received. In some implementations, the preprocessor 501 may normalize the data based on reference data, such as by dividing the received data by reference data. In some implementations, the preprocessor 501 may normalize the data according to equation (7). The preprocessor 501 can output one or more signals indicating optical densities (OD) associated with various wavelengths. The optical densities can be based on filtering, decimating, and/or normalizing the data received at the preprocessor 501.

A hydration engine 503 can receive the signals output from the preprocessor 501, including the optical densities (OD) associated with various wavelengths. The hydration engine 503 can determine a raw hydration index based on the signals received from the preprocessor 501. The hydration engine 503 can determine a raw hydration index based on comparing signals associated with water-dependent wavelengths with signals associated with water-independent wavelengths. The hydration engine 503 can determine a raw hydration index according to any of the example equations described herein. The hydration engine 503 can determine the raw hydration index based on equation (3) and/or equation (4). For example, the hydration engine 503 may subtract an area of a parameter from an area of another parameter. As another example, the hydration engine 503 can normalize the area of a parameter with the area of another parameter. The hydration engine 503 can determine the raw hydration index based on equation (5) and/or equation (6). For example, the hydration engine 503 may subtract a portion of an area of a parameter from a portion of an area of another parameter. As another example, the hydration engine 503 can normalize a portion of an area of a parameter with a portion of an area of another parameter. The hydration engine 503 can determine the raw hydration index based on equation (7) and/or any of equations (8.1)-(8.4). For example, the hydration engine 503 can determine a raw hydration index based on a difference in normalized optical densities.

The hydration engine 503 can determine a raw hydration index (Hi) based on adjusting signals received from detectors. The sensitivity of a detector, such as a photodiode, may vary according to wavelength of radiation detected. A detector may be more sensitive to radiation of a certain wavelength and less sensitive to radiation of another wavelength. The hydration engine 503 can adjust the output of the detector based on wavelength to account for wavelength-based detector sensitivities. For example, the hydration engine 503 may amplify a detector signal corresponding to a wavelength at which the detector is less sensitive. As another example, the hydration engine 503 may not change a detector signal corresponding to a wavelength at which the detector has average sensitivity.

The hydration engine 503 can determine a raw hydration index based on reference hydration information which may also be referred to as a baseline hydration. The hydration engine 503 may further refine the determined raw hydration index by comparing it with the reference hydration information. The reference hydration information can include a plurality of hydration information. The reference hydration information can be derived from, or relate to, the subject. The raw Hi may be a percentage of, or proportional to, the reference hydration. The hydration engine 503 may index the raw Hi to the reference hydration information to further refine the raw Hi. The hydration engine 503 may determine the raw Hi based on a transfer function. The transfer function may be based on the reference hydration information.

The hydration engine 503 can perform measurements and/or determine a raw hydration index periodically. The hydration engine 503 can perform measurements and/or determine a raw hydration index at a specific time. The hydration engine 503 can perform measurements and/or determine a raw hydration index in response to a user request. The hydration engine 503 can output a raw hydration index.

In some implementations, the hydration engine 503 may implement one or more mathematical models to determine the raw Hi. The hydration engine 503 may train the mathematical models using artificial intelligence. The hydration engine 503 may train the mathematical models using one or more of machine learning, neural network, deep learning, transformation functions, or the like.

A post processor 505 can receive the raw Hi from the hydration engine 503. The post processor may further refine the raw Hi to determine a final hydration index (Hi). The post processor 505 may process data received from the hydration engine 303, such as a plurality of raw hydration indices to determine a final Hi. The post processor 505 can average, filter, discard, and/or clean data received from the hydration engine 503 to determine a final Hi. The post processor 505 can determine averages, medians, means, weighted averages, of data received from the hydration engine 503. As an example, the final Hi may be an average, or weighted average of raw hydration indices.

The post processor 505 can determine the final Hi from the raw Hi based on at least calibration data. The post processor 505 can compare data received from the hydration engine 503 with calibration data. The calibration data can include a transfer function. The post processor 505 can apply a transfer function to a raw Hi to determine a final Hi. The calibration data can include a calibration curve. The post processor 505 can apply a calibration curve to a raw Hi to determine a final Hi. The calibration data can include weights. The post processor 505 can apply weights to a raw Hi to determine a final Hi. The calibration data can include an empirical dataset. The empirical dataset may include hydration information of a plurality of subjects. The empirical dataset may include hydration data from a plurality of subjects under controlled conditions, such that the information corresponds to known hydration levels. The empirical dataset may include hydration data from only a single subject such as the user. The post processor 505 may access the calibration data. The calibration data may be stored in memory. The post processor 505 may access the calibration data from a remote computing device such as from a remote server.

Figures 6A, 6B:
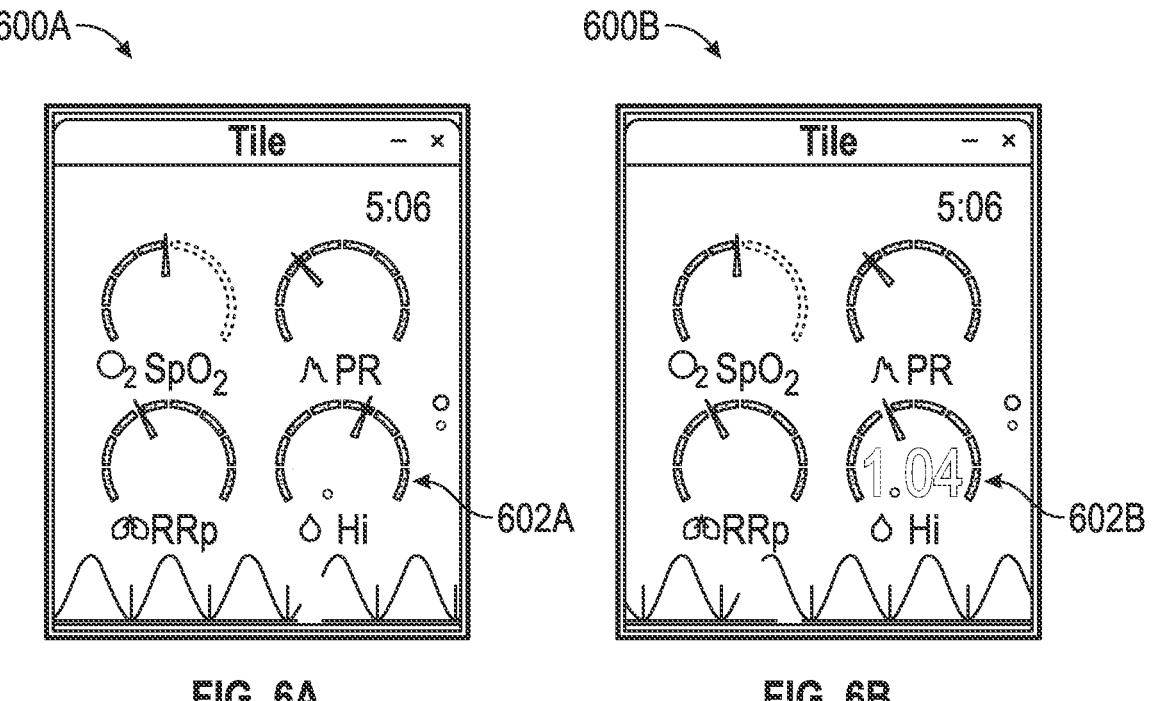
FIGS. 6A-6B illustrate example displays including physiological information such as hydration information.

FIGS. 6A and 6B illustrate example displays 600A and 600B. Displays 600A and 600B can include various physiological parameters of a subject. Displays 600A and 600B can include hydration information such as a hydration index (Hi) 602A and 602B. Hydration index 602A may indicate that a subject is relatively hydrated. Hydration index 602B may indicate that a subject is relatively dehydrated. Portions of the display 600A or 600B and/or the hydration index 602A or 602B may change color based upon the subject's hydration. For example, the number of the hydration index 602B may be displayed in red when the user is dehydrated, while the number of the hydration index 602A may be displayed in white when the user is hydrated.

Terminology

As used herein, "real-time" or "substantial real-time" may refer to events (e.g., receiving, processing, transmitting, displaying etc.) that occur at the same time or substantially the same time (e.g., neglecting any small delays such as those that are imperceptible and/or inconsequential to humans such as delays arising from electrical conduction or transmission). As a non-limiting example, "real-time" may refer to events that occur within a time frame of each other that is on the order of milliseconds, seconds, tens of seconds, or minutes. In some implementations, "real-time" may refer to events that occur at a same time as, or during, another event.

As used herein, "system," "instrument," "apparatus," and "device" generally encompass both the hardware (for example, mechanical and electronic) and, in some implementations, associated software (for example, specialized computer programs for graphics control) components.

It is to be understood that not necessarily all objects or advantages may be achieved in accordance with any particular implementation described herein. Thus, for example, those skilled in the art will recognize that certain implementations may be configured to operate in a manner that achieves or optimizes one advantage or group of advantages as taught herein without necessarily achieving other objects or advantages as may be taught or suggested herein.

Each of the processes, methods, and algorithms described in the preceding sections may be embodied in, and fully or partially automated by, code modules executed by one or more computer systems or computer processors including computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

Many other variations than those described herein will be apparent from this disclosure. For example, depending on the implementation, certain acts, events, or functions of any of the algorithms described herein can be performed in a different sequence, can be added, merged, or left out altogether (for example, not all described acts or events are necessary for the practice of the algorithms). Moreover, in certain implementations, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the implementations disclosed herein can be implemented as electronic hardware, computer software, or combinations of both. To clearly illustrate this interchangeability of hardware and software, various illustrative components, blocks, modules, and elements have been described herein generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various features and processes described herein may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example implementations. The example systems and components described herein may be configured differently than described. For example, elements may be added to, removed from, or rearranged compared to the disclosed example implementations.

The various illustrative logical blocks and modules described in connection with the implementations disclosed herein can be implemented or performed by a machine, such as a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another implementation, a processor includes an FPGA or other programmable devices that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some, or all, of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the implementations disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language, such as, among others, "can," "could," "might," or "may," unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

Disjunctive language such as the phrase "at least one of X, Y, or Z," unless specifically stated otherwise, is otherwise understood with the context as used in general to present that an item, term, and so forth, may be either X, Y, or Z, or any combination thereof (for example, X, Y, and/or Z). Thus, such disjunctive language is not generally intended to, and should not, imply that certain implementations require at least one of X, at least one of Y, or at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 10 degrees, 5 degrees, 3 degrees, or 1 degree. As another example, in certain implementations, the terms "generally perpendicular" and "substantially perpendicular" refer to a value, amount, or characteristic that departs from exactly perpendicular by less than or equal to 10 degrees, 5 degrees, 3 degrees, or 1 degree.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the implementations described herein in which elements or functions may be deleted, executed out of order from that shown or discussed, including substantially concurrently or in reverse order, depending on the functionality involved, as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

All of the methods and processes described herein may be embodied in, and partially or fully automated via, software code modules executed by one or more general purpose computers. For example, the methods described herein may be performed by the computing system and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the herein-described implementations, the elements of which are to be understood as being among other acceptable examples. All such modifications and variations are intended to be included herein within the scope of this disclosure. The section headings used herein are merely provided to enhance readability and are not intended to limit the scope of the implementations disclosed in a particular section to the features or elements disclosed in that section. The foregoing description details certain implementations. It will be appreciated, however, that no matter how detailed the foregoing appears in text, the systems and methods can be practiced in many ways. As is also stated herein, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

What is claimed is:

1. A physiological monitoring system for non-invasively monitoring a subject's hydration, the physiological monitoring system comprising:

a wearable device configured to secure to a subject, the wearable device comprising:

one or more optical emitters configured to emit optical radiation toward a tissue of the subject, wherein the optical radiation includes a water-dependent wavelength and a water-independent wavelength, wherein the water-dependent wavelength is between 900 nm and 1400 nm, wherein the water-independent wavelength is between 600 nm and 700 nm; and one or more optical detectors configured to:

detect the optical radiation emitted by the one or more optical emitters after attenuation through the tissue of the subject; and generate optical data in response to detecting the optical radiation; and one or more hardware computer processors configured to:

access the optical data;

determine a water-dependent optical parameter based on the optical data corresponding to the water-dependent wavelength;

determine a water-independent optical parameter based on the optical data corresponding to the water-independent wavelength;

determine a hydration index of the subject based on normalizing the water-dependent optical parameter with the water-independent optical parameter; and generate user interface data for rendering an indication of the hydration index on a display.

2. The physiological monitoring system of claim 1, wherein normalizing the water-dependent optical parameter with the water-independent optical parameter includes dividing the water-dependent optical parameter by the water-independent optical parameter.

3. The physiological monitoring system of claim 1, wherein normalizing the water-dependent optical parameter with the water-independent optical parameter includes subtracting the water-independent optical parameter from the water-dependent optical parameter.

4. The physiological monitoring system of claim 1, wherein the water-dependent optical parameter corresponds to an optical intensity of the water-dependent wavelength of the optical radiation detected by the one or more optical detectors, and wherein the water-independent optical parameter corresponds to an optical intensity of the water-independent wavelength of the optical radiation detected by the one or more optical detectors.

5. The physiological monitoring system of claim 1, wherein the water-dependent optical parameter corresponds to an absorption of the water-dependent wavelength of the optical radiation by the tissue, and wherein the water-independent optical parameter corresponds to an absorption of the water-independent wavelength of the optical radiation by the tissue.

6. The physiological monitoring system of claim 1, wherein the water-dependent wavelength of the optical radiation is sensitive to absorption by water, and wherein absorption of the water-independent wavelength of the optical radiation is substantially unaffected by water.

7. The physiological monitoring system of claim 1, wherein the one or more hardware computer processors is further configured to:

access reference optical data corresponding to other radiation attenuated through a reference medium, wherein the other radiation includes the water-dependent wavelength and water-independent wavelength;

determine the water-dependent optical parameter based on normalizing the optical data corresponding to the water-dependent wavelength with the reference optical data corresponding to the water-dependent wavelength; and determine the water-independent optical parameter based on normalizing the optical data corresponding to the water-independent wavelength with the reference optical data corresponding to the water-independent wavelength.

8. The physiological monitoring system of claim 7, wherein the optical data corresponds to an optical density of the tissue, and wherein the reference optical data corresponds to an optical density of the reference medium.

9. The physiological monitoring system of claim 1, wherein the one or more hardware computer processors is further configured to:

determine a second water-dependent optical parameter based on a second water-dependent wavelength of the optical radiation;

determine a second water-independent optical parameter based on a second water-independent wavelength of the optical radiation; and determine the hydration index based on normalizing a difference between the water-dependent optical parameter and the second water-dependent optical parameter with a difference between the water-independent optical parameter and the second water-independent optical parameter.

10. The physiological monitoring system of claim 9, wherein the second water-dependent wavelength of the optical radiation is between 900 nm and 1000 nm.

11. The physiological monitoring system of claim 9, wherein the second water-independent wavelength of the optical radiation is between 600 nm and 700 nm.

12. The physiological monitoring system of claim 9, wherein the water-dependent optical parameter corresponds to an estimated area integrated under an absorption curve between the water-dependent wavelength and the second water-dependent wavelength.

13. The physiological monitoring system of claim 9, wherein the water-independent optical parameter corresponds to an estimated area integrated under an absorption curve between the water-independent wavelength and the second water-independent wavelength.

14. The physiological monitoring system of claim 1, wherein the one or more hardware computer processors is further configured to:

access reference optical data corresponding to other radiation attenuated through a reference medium, wherein the other radiation includes the water-dependent wavelength, a second water-dependent wavelength, the water-independent wavelength, and a second water-independent wavelength, wherein the optical radiation includes the second water-dependent wavelength and the second water-independent wavelength;

determine the water-dependent optical parameter based on normalizing the optical data corresponding to the water-dependent wavelength with the reference optical data corresponding to the water-dependent wavelength;

determine a second water-dependent optical parameter based on normalizing the optical data corresponding to the second water-dependent wavelength with the reference optical data corresponding to the second water-dependent wavelength;

determine the water-independent optical parameter based on normalizing the optical data corresponding to the water-independent wavelength with the reference optical data corresponding to the water-independent wavelength;

determine a second water-independent optical parameter based on normalizing the optical data corresponding to the second water-independent wavelength with the reference optical data corresponding to the second water-independent wavelength; and determine the hydration index of the tissue based on normalizing a difference between the water-dependent optical parameter and the second water-dependent optical parameter with a difference between the water-independent optical parameter and the second water-independent optical parameter.

15. The physiological monitoring system of claim 14, wherein the water-dependent wavelength of the optical radiation is 970 nm, wherein the second water-dependent wavelength of the optical radiation is 905 nm, wherein the water-independent wavelength of the optical radiation is 620 nm, and wherein the second water-independent wavelength of the optical radiation is 660 nm.

16. A method of non-invasively monitoring a subject's hydration, the method comprising:

emitting, by one or more optical emitters, optical radiation toward a tissue of a subject, wherein the optical radiation includes a water-dependent wavelength and a water-independent wavelength, wherein the water-dependent wavelength is between 900 nm and 1400 nm, wherein the water-independent wavelength is between 600 nm and 700 nm;

detecting, by one or more optical detectors, the optical radiation emitted after attenuation through the tissue of the subject;

generating optical data in response to detecting the optical radiation;

determining a water-dependent optical parameter based on the optical data corresponding to the water-dependent wavelength;

determining a water-independent optical parameter based on the optical data corresponding to the water-independent wavelength;

determining a hydration index of the subject based on normalizing the water-dependent optical parameter with the water-independent optical parameter;

generating user interface data for rendering an indication of the hydration index on a display; and displaying, via the display, the indication of the hydration index.

17. The method of claim 16 further comprising:

determining a second water-dependent optical parameter based on a second water-dependent wavelength of the optical radiation;

determining a second water-independent optical parameter based on a second water-independent wavelength of the optical radiation; and determining the hydration index based on normalizing a difference between the water-dependent optical parameter and the second water-dependent optical parameter with a difference between the water-independent optical parameter and the second water-independent optical parameter.

18. The method of claim 17, wherein the second water-dependent wavelength of the optical radiation is between 900 nm and 1000 nm.

19. Non-transitory computer-readable media including computer-executable instructions that, when executed by a computing system, cause the computing system to perform operations comprising:

emitting, by one or more optical emitters, optical radiation toward a tissue of a subject, wherein the optical radiation includes a water-dependent wavelength and a water-independent wavelength, wherein the water-dependent wavelength is between 900 nm and 1400 nm, wherein the water-independent wavelength is between 600 nm and 700 nm;

detecting, by one or more optical detectors, the optical radiation emitted after attenuation through the tissue of the subject;

generating optical data in response to detecting the optical radiation;

determining a water-dependent optical parameter based on the optical data corresponding to the water-dependent wavelength;

determining a water-independent optical parameter based on the optical data corresponding to the water-independent wavelength;

determining a hydration index of the subject based on normalizing the water-dependent optical parameter with the water-independent optical parameter;

generating user interface data for rendering an indication of the hydration index on a display; and displaying, via the display, the indication of the hydration index.

20. The non-transitory computer-readable media of claim 19, wherein the computer-executable instructions, when executed by the computing system, cause the computing system to perform operations comprising:

determining a second water-dependent optical parameter based on a second water-dependent wavelength of the optical radiation;

determining a second water-independent optical parameter based on a second water-independent wavelength of the optical radiation; and determining the hydration index based on normalizing a difference between the water-dependent optical parameter and the second water-dependent optical parameter with a difference between the water-independent optical parameter and the second water-independent optical parameter.

* * * * *